(12) United States Patent
Basati et al.

(10) Patent No.: US 11,511,026 B2
(45) Date of Patent: Nov. 29, 2022

(54) DIALYSIS AND METHODS INCLUDING SENSOR FEEDBACK TO IMPROVE PATIENT EXPERIENCE

(71) Applicants: BAXTER INTERNATIONAL INC., Deerfield, IL (US); BAXTER HEALTHCARE SA, Glattpark (CH)

(72) Inventors: Sukhraaj Basati, Bartlett, IL (US); Shantanu Avinash Gadre, Palatine, IL (US); Mohammad Ali Jamnia, Pleasant Prairie, WI (US); Lakshmy M. Nair, Vernon Hills, IL (US); William J. O'Reilly, Waukesha, WI (US); Marta Wlodarczyk, Arlington Heights, IL (US)

(73) Assignees: Baxter International Inc., Deerfield, IL (US); Baxter Healthcare SA, Glattpark (CH)

( * ) Notice: Subject to any disclaimer, the term of this patent is extended or adjusted under 35 U.S.C. 154(b) by 435 days.

(21) Appl. No.: 16/522,229

(22) Filed: Jul. 25, 2019

(65) Prior Publication Data
US 2020/0030517 A1  Jan. 30, 2020

Related U.S. Application Data

(60) Provisional application No. 62/703,749, filed on Jul. 26, 2018.

(51) Int. Cl.
*A61M 1/28* (2006.01)
*A61M 1/16* (2006.01)

(52) U.S. Cl.
CPC ............ *A61M 1/284* (2014.02); *A61M 1/285* (2013.01); *A61M 1/287* (2013.01); *A61M 1/166* (2014.02);
(Continued)

(58) Field of Classification Search
CPC ........ A61M 1/28; A61M 1/281; A61M 1/282; A61M 1/283; A61M 1/284; A61M 1/285;
(Continued)

(56) References Cited

U.S. PATENT DOCUMENTS

| 2010/0021878 A1* | 1/2010 | Kim | ..................... G01N 15/147 435/2 |
| 2013/0122528 A1* | 5/2013 | Tyrell | ................. G01N 33/6893 435/7.92 |

(Continued)

FOREIGN PATENT DOCUMENTS

WO    2017092871    6/2017

OTHER PUBLICATIONS

International Search Report; PCT/US2019/043450 dated Dec. 16, 2019— 10 pages.
(Continued)

*Primary Examiner* — Kami A Bosworth
(74) *Attorney, Agent, or Firm* — K&L Gates LLP

(57) ABSTRACT

Peritoneal dialysis, such as automated peritoneal dialysis ("APD") is provided with any one or more or all of the following sensing or feedback features: impedance sensing to detect peritonitis, temperature sensing to detect peritonitis, bio-MEMS sensing to detect peritonitis, and glucose control for diabetes patients, wherein each sensing or feedback feature analyzes patient effluent fluid or fluid dwelling within a patient's peritoneal cavity.

20 Claims, 14 Drawing Sheets

(52) U.S. Cl.
CPC .......... *A61M 1/288* (2014.02); *A61M 2205/52* (2013.01)

(58) Field of Classification Search
CPC .......... A61M 1/287; A61M 2205/3303; A61M 2205/3317; A61M 2205/3327; A61M 2205/52; A61M 2210/1017; A61M 2230/201; A61M 2230/65; A61B 5/05; A61B 5/0538; A61B 5/14532; A61B 5/150992
See application file for complete search history.

(56) References Cited

U.S. PATENT DOCUMENTS

| | | | |
|---|---|---|---|
| 2014/0018727 A1* | 1/2014 | Burbank ............. | A61M 1/1672 604/28 |
| 2015/0088047 A1 | 3/2015 | Gerber et al. | |
| 2018/0043080 A1 | 2/2018 | Gerber et al. | |

OTHER PUBLICATIONS

Written Opinion; PCT/US2019/043450 dated Dec. 16, 2019—12 pages.

IPRP Appln. No. PCT/US2019/043450 dated Sep. 28, 2020—11 pages.

\* cited by examiner

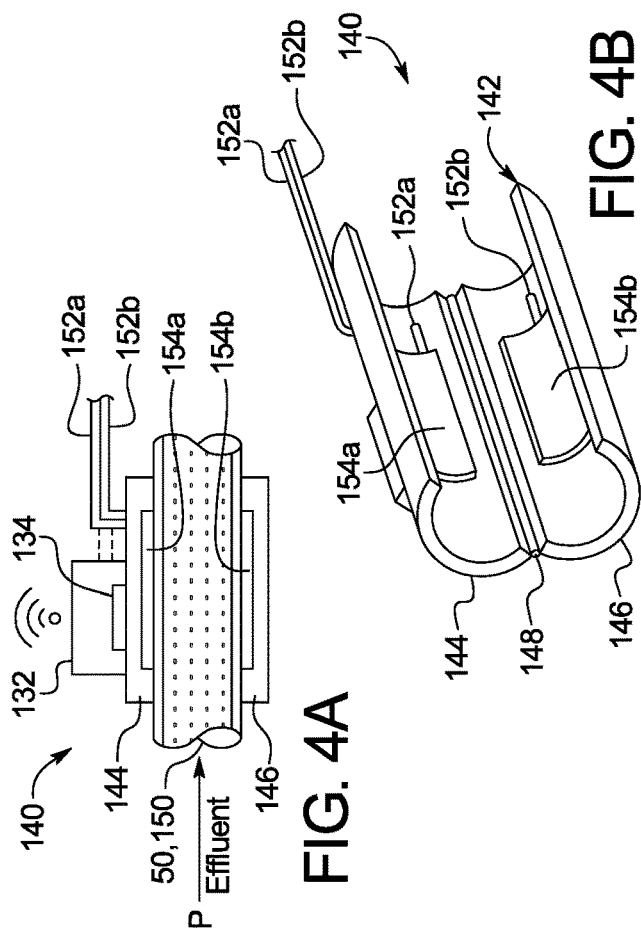
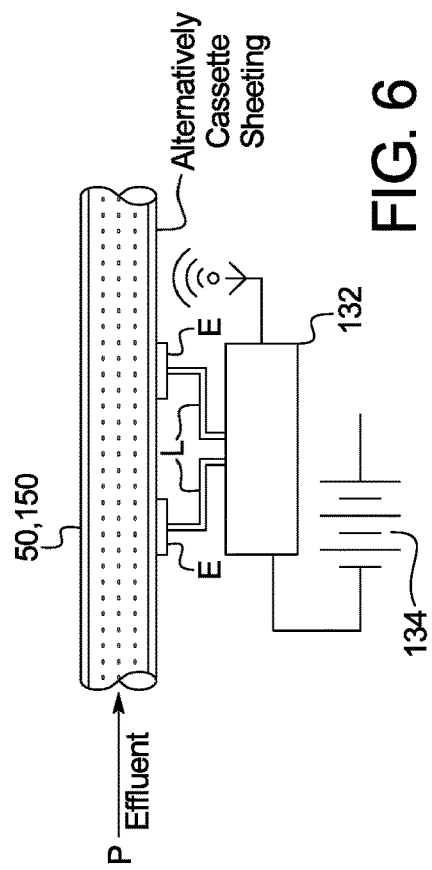
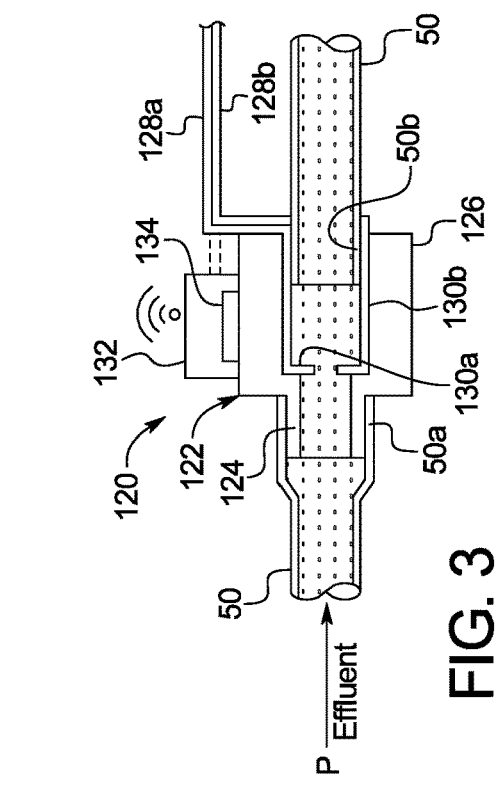
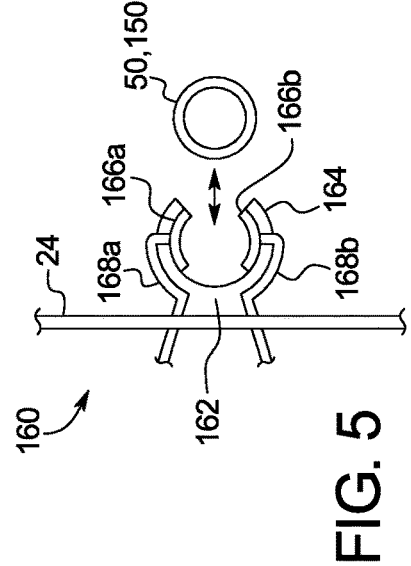

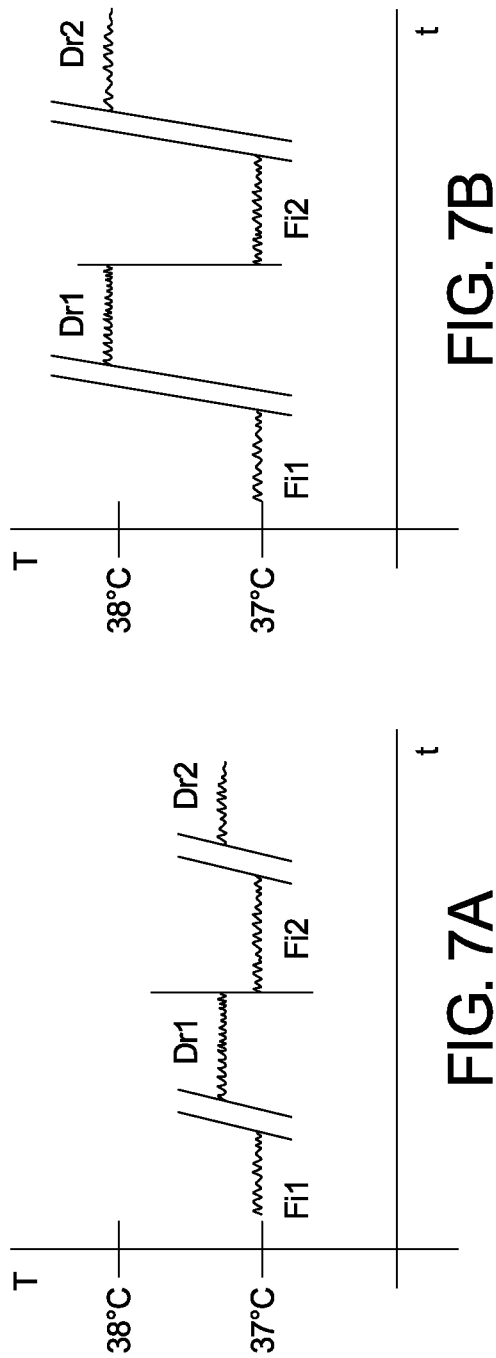
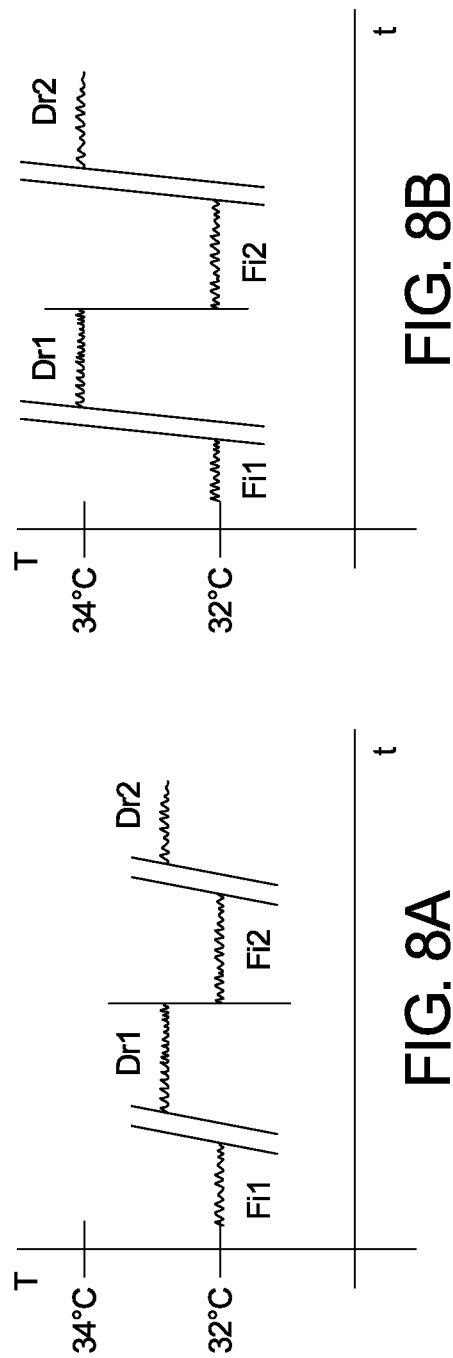

DIALYSIS AND METHODS INCLUDING SENSOR FEEDBACK TO IMPROVE PATIENT EXPERIENCE

PRIORITY CLAIM

This application is a non-provisional application claiming priority to and the benefit of provisional U.S. Patent Application No. 62/703,749, filed Jul. 26, 2018, entitled "Dialysis Systems And Methods Including Sensor Feedback To Improve Patient Experience", the entire contents of which are incorporated herein by reference and relied upon.

BACKGROUND

The present disclosure relates generally to the treatment of end stage renal disease. More specifically, the present disclosure relates to methods and apparatuses for monitoring and/or controlling the performance of peritoneal dialysis.

Using dialysis to support a patient whose renal function has decreased to the point where the kidneys no longer sufficiently function is known. Two principal dialysis methods are provided, namely, hemodialysis; and peritoneal dialysis.

In hemodialysis, the patient's blood is passed through an artificial kidney dialysis machine. A membrane in the machine acts as an artificial kidney for cleansing the blood. Because it is an extracorporeal treatment requiring special machinery, certain inherent disadvantages exist with hemodialysis. To overcome disadvantages associated with hemodialysis, peritoneal dialysis has been developed. Peritoneal dialysis uses the patient's own peritoneum as a semi-permeable membrane. The peritoneum is a membranous lining of the patient's abdominal body cavity. Due to good perfusion, the peritoneum acts as a natural semi-permeable membrane.

Peritoneal dialysis periodically infuses a sterile aqueous solution or dialysis fluid into the peritoneal cavity. Diffusion and osmotic exchanges take place between the peritoneal dialysis fluid and the blood stream across the natural body membranes. The exchanges remove the waste products that the kidneys normally excrete. The waste products consist of solutes like urea and creatinine. The kidneys also maintain the levels of other substances such as sodium and water. Dialysis regulates the diffusion of water and solutes across the peritoneal membrane during dialysis, which is called ultrafiltration.

In continuous ambulatory peritoneal dialysis ("CAPD"), a dialysis solution is introduced into the peritoneal cavity via a catheter. An exchange of solutes between the dialysis fluid and the blood is achieved by diffusion. Further solute removal is achieved via the dialysis fluid providing a suitable osmotic gradient from the blood to the dialysis fluid. The osmotic gradient allows a proper acid-base, electrolyte and fluid balance to be achieved in the patient's body. Used dialysis fluid or effluent fluid is drained manually via gravity from the body cavity through the catheter.

A variation of CAPD is automated peritoneal dialysis ("APD"). APD uses a machine, called a cycler, to automatically infuse, dwell, and drain peritoneal dialysis fluid to and from the patient's peritoneal cavity. APD is attractive to a peritoneal dialysis patient because it may be performed at night while the patient is asleep, which frees the patient from the day-to-day demands of CAPD during his/her waking and working hours.

The APD sequence typically lasts for several hours. It often begins with an initial drain phase to empty the peritoneal cavity of spent dialysis fluid from the prior treatment. The APD sequence then proceeds through a succession of fill, dwell, and drain phases that follow one after the other. Each fill/dwell/drain sequence is called a cycle.

The proportion of patients performing automated peritoneal dialysis ("APD") is increasing worldwide, which is due in part to the ability of APD to be adapted to the patient's particular needs regarding the patient's private life and the patient's therapy needs. The two primary goals of dialysis, solute clearance and ultrafiltration ("UF") depend on the modality or type of APD performed (e.g., nocturnal intermittent peritoneal dialysis ("NIPD"), continuous cycling peritoneal dialysis ("CCPD") and hi-dose CCPD), the solution type, the therapy time and the fill volume. Prescribing an APD therapy constitutes selecting one of each of these. Thus there are many combinations and possibilities from which to choose.

APD devices typically do not have the capability to provide feedback to the patient regarding the effectiveness of his/her recent therapies. Also, APD devices typically run open loop such that they do not adjust therapy parameters (e.g., modality, solution type, therapy time and fill volume) based on the actual measured daily clearance and UF. Accordingly, some patients underachieve their targets and develop adverse conditions such as fluid overload and in some cases hypertension. Current methods for adjusting treatment typically involve the patient reporting to a center every so often to be evaluated. These methods place the burden of therapy adjustment solely on the doctor or clinician and do not occur frequently enough to adjust properly to the patient's weekly, monthly, seasonal or other lifestyle change.

APD, like CAPD, uses a catheter implanted in the patient's peritoneum to deliver fresh dialysis fluid to and to remove used dialysis fluid from the patient's peritoneal cavity. The placement of the peritoneal catheter provides an opportunity to sense desired parameters within the patient. Additionally, APD and CAPD both remove used or effluent PD fluid from the patient, which provides opportunities to sense patient parameters or characteristics residing within the effluent fluid. A need accordingly exists to provide systems and methods that take advantage of the placement of the patient catheter and/or the effluent PD fluid removed from the patient to help monitor and/or control a peritoneal dialysis treatment, such as CAPD and APD. And more generally, a need exists for immediate or in-treatment feedback to help with various problems associated with peritoneal dialysis.

SUMMARY

The examples described herein disclose systems and methods for improved peritoneal dialysis ("PD") treatment. Three of the systems and methods described herein involve detection and optimally early detection of peritonitis. Peritonitis is an inflammation of the peritoneum, which is the tissue that lines the inner wall of the abdomen and covers and supports most of the abdominal organs. The peritoneal wall is also the membrane used for peritoneal dialysis as described above. Peritonitis is usually caused by infection from bacteria or fungi, which may enter through the patient's peritoneal catheter.

Left untreated, peritonitis can rapidly spread into the blood (sepsis) and other organs, resulting in multiple organ failure and death. The first symptoms of peritonitis are typically poor appetite and nausea and a dull abdominal ache that quickly turns into persistent, severe abdominal pain.

Other signs and symptoms related to peritonitis may include: abdominal tenderness or distention, chills, fever, fluid in the abdomen, and vomiting.

The death rate from peritonitis depends on many factors, but can be as high as 40% in those who also have cirrhosis. As many as 10% may die from secondary peritonitis. Primary spontaneous peritonitis is an infection that develops in the peritoneum and is the type associated with peritoneal dialysis treatment. Secondary peritonitis usually develops when an injury or infection in the abdominal cavity allows infectious organisms into the peritoneum. Both types of peritonitis are life-threatening.

Current methods for determining peritonitis are subjective and place the burden on the patient. For example, patients may be told to observe the color and/or texture of their effluent fluid to look for peritonitis. Or, patients may be told to be aware of a full stomach feeling and/or fever. When the patient thinks peritonitis is oncoming or present, the patient has to bring an effluent sample to the clinic for testing. The above methods are subjective and place the burden on the patient. The below systems and methods are automatic and objective.

Temperature Sensing for Peritonitis

In one primary embodiment, the temperature of used dialysis fluid exiting the patient is measured to detect peritonitis. In healthy patients, the temperature of used dialysis fluid is normal body temperature or about 37° C. In patients experiencing the onset of peritonitis, the used dialysis fluid exiting the patient may reside at an elevated temperature. The system and method of the first primary embodiment measure the effluent dialysis fluid and use the measurement to make a determination as to whether the patient may be experiencing the onset of peritonitis.

The temperature measurement may be made in a number of different ways. In one way, a temperature sensor, such as a thermocouple or thermistor is placed in a connector, such as a clamshell type connector, which clips removeably and selectively over the patient line. The clamshell connector may be placed in any desired location around the patient line, for example, near the patient so that the temperature of the patient's effluent dialysis fluid may be taken immediately upon leaving the patient. In one embodiment, the temperature of the effluent fluid is compared to the temperature of the fresh dialysis fluid, which may be heated to body temperature or 37° C. In this manner, any temperature offset caused by the generally non-thermally conductive tubing is negated. For example, if the temperature of the 37° C. fresh dialysis fluid is read through the tubing at an offset temperature of 32° C., the same offset will be assumed for the effluent fluid leaving the patient. The control unit reading the temperature signal will therefore look for a 32° C. patient healthy signal and will trigger a potential peritonitis alert when the control unit sees a signal indicating a temperature above 32° C.

In an alternative embodiment, a more thermally conductive and medically safe material, such as stainless steel is spliced or fitted into the patient line. One or more thermally conductive electrode is attached to the temperature sensor and allows for a more accurate temperature reading. Here, the control unit reading the temperature signal looks in one embodiment for a 37° C. patient healthy signal and triggers a potential peritonitis alert when the control unit sees a signal indicating a temperature above 37° C. In this example, the control unit may or may not take the incoming temperature of fresh dialysis fluid into account.

In any embodiment in which the temperature sensor is located remote from the cycler, the temperature sensor may send the measured signals in a wired or wireless manner to the cycler for interrogation. The temperature sensor is in one embodiment a passive device (e.g., two wires creating voltage based upon fluid temperature). If the temperature sensor does require power, power may be provided via a battery or from the cycler or a water purifier operating with the cycler via power wires.

In a further alternative embodiment, the temperature sensor, e.g., thermocouple or thermistor, is located within the dialysis machine or cycler and operates with the disposable cassette or the patient line extending from the disposable cassette. The temperature sensor contacts the flexible sheeting of the disposable cassette in one or more places in one embodiment. One or more thermally conductive contact may be formed in or added to the disposable cassette to help temperature sensing accuracy. As above, when sensing at or near the cassette, the control unit may or may not take the incoming temperature of fresh dialysis fluid into account.

Temperature sensing is performed alternatively in a drain line extending from the disposable cassette. The drain line is advantageous because sterility is less of an issue, such that the drain line is in one embodiment plugged into a reusable thermally conductive contact provided with the cycler or with a water purification device operating with the cycler.

The control unit is programmed in one embodiment to alert the patient at the user interface of the cycler if an elevated temperature indicating peritonitis is detected. Alternatively or additionally, the control unit operates via a network and one or more server computer to enable a doctor or clinician to view effluent temperature data, e.g., on an ongoing basis, so that the clinician may determine if the patient is at risk of peritonitis. The data is displayed in one embodiment on a dashboard of a website for the patient, wherein the temperature data may be presented with a flag for the clinician when it is elevated, indicating peritonitis.

Bio-MEMS Sensing for Peritonitis

In a second primary embodiment, which may be used alternatively or in addition to the first embodiment, a bio-Micro-Electro-Mechanical-System ("bio-MEMS") sensor is used to detect peritonitis. The bio-MEMS sensor is used to look for the presence of white blood cells from the patient in the effluent, which is an indicator of peritonitis. In one implementation, effluent fluid from the cycler is pumped to drain. The drain line is connected to a lab-on-chip diagnostic detection device. The lab-on-chip or bio-MEMS device includes a container into which a sampling line extends, wherein the sampling line may extend or tee off of the drain line. The effluent sample entering the container of the bio-MEMS device first encounters a microfluidic pathway that splits the patient's white blood cells from the effluent fluid. The white blood cells are then weighed using a piezoelectric biosensor in one embodiment. The piezoelectric biosensor resonates with a frequency proportional to a change in the deposition rate of white blood cells.

The bio-MEMS device is placed alternatively in the patient line via a sample line and used to analyze effluent returning from the patient. In this manner, the bio-MEMS device may be used to sense fresh dialysis fluid delivered to the patient additionally if desired.

In one embodiment, the bio-MEMS device includes the electronics and processing to process raw signals from the piezoelectric biosensor and make a determination as to the presence or not of white blood cells. The bio-MEMS device may also include a user interface to indicate to the patient or caregiver present during treatment weather or not there is an indication of peritonitis. In an alternative embodiment, either one or both of (i) electronics and processing to process raw signals from the piezoelectric biosensor or (ii) the user interface for patient or caregiver communication may be provided instead by the cycler or perhaps a water purification device operable with the cycler.

As with the first primary embodiment, the control unit and processing for the second primary embodiment may alternatively or additionally operate via a network and one or more server computer to enable a doctor or clinician to view bio-MEMS data, e.g., on an ongoing basis, so that the clinician may determine if the patient is at risk of peritonitis. The data of the second primary embodiment may be displayed in combination with the data of the first primary embodiment to provide a combination of peritonitis indicators.

Impedance Monitoring for Peritonitis

In a third primary embodiment, which may be used alternatively or in addition to the first embodiment and/or the second embodiment, an impedance monitor is used to detect peritonitis. The impedance monitor is used to look for the presence of white blood cells from the patient in the effluent fluid, which again is an indicator of peritonitis. In various implementations, the impedance monitor may be placed anywhere that the patient's effluent fluid may be sensed, for example, in the patient's indwelling catheter, along the patient line or anywhere along the drain line. In any of these locations, the catheter or line is fitted with electrodes, e.g., in any of the ways discussed above for temperature sensing, but with the goal now of placing electrically conductive contacts in communication with the effluent dialysis fluid.

An electrically conductive and medically safe material, such as stainless steel, is spliced or fitted into the catheter, patient line or drain line in one embodiment, e.g., via a clamshell connector or a connector that is spliced into the drain line. The control unit controlling the impedance monitor in one embodiment causes an electrical frequency sweep to be generated in the effluent fluid. Such impedance spectroscopy (or obtaining complex impedance) may provide additional details about the content(s) of the effluent fluid. For example, the electrical properties of fibrin (normal, not indicating peritonitis) may vary from the electrical properties of white blood cells (indicating peritonitis). Once the electrical properties of different substances within the effluent fluid are learned, the properties may be programmed into the control unit and used thereafter to determine what if anything is entrained in the effluent dialysate stream.

In any embodiment in which the impedance monitor is located remote from the cycler, the impedance monitor may send the measured signals in a wired or wireless manner to the cycler for interrogation. The impedance monitor as mentioned above has the ability to emit a frequency sweep into the effluent fluid and thus may receive power either via a battery or from the cycler or a water purifier operating with the cycler via power wires.

In an alternative embodiment, the impedance monitor is located within the dialysis machine or cycler and operates with the disposable cassette or the patient or drain line extending from the disposable cassette. The impedance monitor extends through a rigid wall holding the disposable cassette sheeting in one or more places in one embodiment. In a further alternative embodiment, the impedance monitor is operable with the drain line located within a water purifier supplying purified water to the dialysis machine or cycler.

The control unit is programmed in one embodiment to alert the patient or caregiver at the user interface of the cycler if white blood cells indicating peritonitis are detected. Alternatively or additionally, the control unit operates via a network and one or more server computer to enable a doctor or clinician to view effluent impedance data, e.g., on an ongoing basis, so that the clinician may determine if the patient is at risk of peritonitis. The data is displayed in one embodiment on a dashboard of a website for the patient, wherein the effluent impedance data may be presented with a flag for the clinician when white blood cells are present, indicating peritonitis. The data of the third primary embodiment may be displayed in combination with the data of the first and/or second primary embodiments to provide a combination of peritonitis indicators.

When the impedance monitor is placed in the indwelling catheter or in the patient line via a sample line and used to analyze effluent within the patient or returning from the patient, the impedance monitor may be used to sense fresh dialysis fluid delivered to the patient additionally if desired. When the impedance monitor is placed in the drain line, it may be used additionally to detect if dialysis fluid made at the point of use has been mixed properly.

Glucose Control for Diabetic Patients

Glucose (or dextrose) is the primary osmotic agent used with most PD solutions. The absorption of most of the peritoneal glucose load over a dwell period may have a detrimental effect on patients suffering from diabetes. Diabetes is a common cause of kidney failure leading to the need for dialysis treatment. In addition, daily exposure to glucose may induce hyperglycemia in PD patients, which can have serious consequences. Certain diabetic PD patients accordingly receive insulin with their PD treatment to help maintain a glucose balance. Patients receiving insulin with PD treatment, however, run the risk of trying to match the amount of insulin to the amount of PD treatment received.

In a fourth primary embodiment, which may be used alternatively or in addition to the first, second and/or third primary embodiments, a bio-MEMS-insulin system and method are provided to match the amount of insulin to the amount of PD fluid used. The bio-MEMS-insulin system and method measures the glucose level of the effluent dialysis fluid leaving the patient. That measurement is then used to properly dose the patient with insulin for the next patient PD fill. In one embodiment, the patient is full of fluid from the previous treatment when beginning the current treatment. That effluent fluid is removed and at least a portion of which is delivered to a MEMS affinity glucose sensor, which sends a signal to a control unit, which determines how much insulin to deliver to a PD supply volume to form a desired concentration of insulin for the initial fill. The corresponding amount of insulin is then delivered to a PD fluid supply bag to yield the desired concentration.

The MEMS affinity glucose sensor is used in one embodiment to measure glucose in the drained effluent. In one implementation, effluent fluid from the cycler is pumped to drain. The drain line is connected fluidically to the MEMS affinity glucose sensor. The MEMS affinity glucose sensor includes a container into which a sampling line extends, wherein the sampling line may extend or tee off of the drain line. The effluent sample entering the container of the MEMS affinity glucose sensor first encounters a microfluidic pathway that splits the glucose molecules from the effluent fluid. The glucose molecules are then weighed using a piezoelectric biosensor in one embodiment. The piezoelectric biosensor resonates with a frequency proportional to a change in the deposition rate of glucose molecules. Glucose absorbed at the end of an nth cycle is calculated using the equation for $A_n$ discussed below. To compensate for the absorbed glucose for the nth cycle, the administration of the insulin dosage during the subsequent cycle would be calculated using an equation for $I_{n+1}$ discussed below.

The MEMS affinity glucose sensor in one embodiment includes the electronics and processing to process raw signals from the piezoelectric biosensor and make a determination as to the proper concentration of insulin to prepare with the PD solution. The MEMS affinity glucose sensor may also include a user interface to indicate to the patient or caregiver present during treatment that the proper insulin level is being determined. In alternative embodiments, either one or both of (i) electronics and processing to process raw signals from the piezoelectric biosensor or (ii) the user interface for patient or caregiver communication are provided instead by the cycler or perhaps a water purification device operable with the cycler. The PD cycler may operate with pre-prepared PD dialysis fluid or with PD dialysis fluid prepared at the point of use. With pre-prepared PD dialysis fluid, insulin is added to a heater bag or to an insulin port on the bag of the solution. With PD dialysis fluid prepared at the point of use, insulin may be added to the mixed dialysis fluid or to any component thereof (purified water, osmotic agent or electrolyte).

the control unit of the cycler operates via a network and one or more server computer in one embodiment to enable a doctor or clinician to view insulin usage data, e.g., on a per-treatment basis, so that the clinician may confirm that insulin is being delivered properly. The data is displayed in one embodiment on a dashboard of a website for the patient, wherein the insulin volume and concentration with PD fluid may be viewed. The data of the fourth primary embodiment may be displayed in combination with the data of the first, second and/or third primary embodiments to provide a desired combination of data.

In light of the disclosure herein and without limiting the disclosure in any way, in a first aspect of the present disclosure, which may be combined with any other aspect listed herein unless specified otherwise, a peritoneal dialysis ("PD") system includes: a cycler including a pump actuator and a control unit in operable communication with the pump actuator; a disposable set including a disposable cassette having a pump chamber, the disposable cassette sized and arranged to be held by the cycler such that the pump chamber is in operable communication with the pump actuator, the disposable set including a patient line and a drain line extending from the disposable cassette; and a temperature sensor operably coupled to one of the patient line, drain line or disposable cassette to sense a temperature of effluent PD fluid removed from a patient, the sensed temperature used to form a patient peritonitis determination, the control unit configured to communicate the peritonitis determination.

In a second aspect of the present disclosure, which may be combined with any other aspect listed herein unless specified otherwise, the sensed temperature is sent to the control unit, and wherein the control unit is configured to analyze the sensed temperature.

In a third aspect of the present disclosure, which may be combined with the second aspect in combination with any other aspect listed herein unless specified otherwise, the sensed temperature is sent to the control unit wired or wirelessly.

In a fourth aspect of the present disclosure, which may be combined with any other aspect listed herein unless specified otherwise, the PD system includes a network and at least one doctor or clinician computer in communication with the control unit via the network, the control unit configured to communicate the peritonitis determination to at least one of a patient or caregiver via a user interface of the cycler or the at least one doctor or clinician computer via the network.

In a fifth aspect of the present disclosure, which may be combined with any other aspect listed herein unless specified otherwise, the PD system includes a water purifier configured to supply purified water to the disposable set, the water purifier including a water purifier control unit, wherein the sensed temperature is sent to the water purifier control unit, wherein the water purifier control unit is configured to analyze the sensed temperature, and wherein the cycler control unit and the water purifier control unit are in communication to allow the cycler control unit to communicate the peritonitis determination.

In a sixth aspect of the present disclosure, which may be combined with the fifth aspect in combination with any other aspect listed herein unless specified otherwise, either the cycler control unit or the water purifier control unit is configured to analyze the sensed temperature.

In a seventh aspect of the present disclosure, which may be combined with any other aspect listed herein unless specified otherwise, the temperature sensor is placed in a connector configured to couple to the patient line or the drain line.

In an eighth aspect of the present disclosure, which may be combined with the seventh aspect in combination with any other aspect listed herein unless specified otherwise, the connector is (i) a clamshell connector that fits around the patient line or the drain line or (ii) configured to be spliced between two sections of the patient line or the drain line.

In a ninth aspect of the present disclosure, which may be combined with the seventh aspect in combination with any other aspect listed herein unless specified otherwise, the connector includes electrodes positioned and arranged to contact (a) effluent fluid flowing through the patient line or the drain line or (b) the patient line or the drain line directly.

In a tenth aspect of the present disclosure, which may be combined with the ninth aspect in combination with any other aspect listed herein unless specified otherwise, in (b) a thermally conductive segment is spliced between sections of the patient line or the drain line, the connector connected directly to the thermally conductive segment.

In an eleventh aspect of the present disclosure, which may be combined with the ninth aspect in combination with any other aspect listed herein unless specified otherwise, the connector includes leads extending from the electrodes to (i) the control unit, (ii) a control unit of a water purifier configured to supply purified water to the disposable set, or (iii) a wireless module provided with the connector.

In a twelfth aspect of the present disclosure, which may be combined with any other aspect listed herein unless specified otherwise, the PD system is configured to analyze the sensed temperature of the effluent PD fluid removed from the patient by comparing the sensed temperature to a temperature of fresh PD fluid delivered to the patient and sensed by the temperature sensor.

In a thirteenth aspect of the present disclosure, which may be combined with any other aspect listed herein unless specified otherwise, the PD system is configured to analyze the sensed temperature of the effluent PD fluid removed from the patient by looking for an increase in temperature due to peritonitis or the onset thereof.

In a fourteenth aspect of the present disclosure, which may be combined with the thirteenth aspect in combination with any other aspect listed herein unless specified otherwise, the increase in temperature due to peritonitis or the onset thereof is detectable regardless of whether the sensed temperature is offset due to sensing through the patient line, the drain line or the disposable cassette.

In a fifteenth aspect of the present disclosure, which may be combined with any other aspect listed herein unless specified otherwise, the peritonitis determination is a first peritonitis indicator, and which includes at least one different peritonitis indicator useable in combination with the first peritonitis indicator to form an overall peritonitis determination.

In a sixteenth aspect of the present disclosure, which may be combined with the fifteenth aspect in combination with any other aspect listed herein unless specified otherwise, the at least one different peritonitis indicator useable in combination with the first peritonitis indicator is obtained from at least one of a white blood cell biosensor or a white blood cell impedance sensor.

In a seventeenth aspect of the present disclosure, which may be combined with any other aspect listed herein unless specified otherwise, the peritonitis determination is provided in combination with insulin injection made using feedback from a patient effluent glucose biosensor.

In an eighteenth aspect of the present disclosure, which may be combined with any other aspect listed herein unless specified otherwise, a peritoneal dialysis ("PD") system includes: a cycler including a pump actuator and a control unit in operable communication with the pump actuator; a disposable set including a disposable cassette having a pump chamber, the disposable cassette sized and arranged to be held by the cycler such that the pump chamber is in operable communication with the pump actuator; and a bio-MEMS device in fluid communication with the disposable cassette, the bio-MEMS device configured to collect white blood cells from effluent PD fluid removed from a patient, the collected white blood cells used to form a patient peritonitis determination, the control unit configured to communicate the peritonitis determination.

In a nineteenth aspect of the present disclosure, which may be combined with the eighteenth aspect in combination with any other aspect listed herein unless specified otherwise, an indication of the collected white blood cells is sent to the control unit, and wherein the control unit is configured to analyze the indication of the collected white blood cells.

In a twentieth aspect of the present disclosure, which may be combined with the nineteenth aspect in combination with any other aspect listed herein unless specified otherwise, the indication of the collected white blood cells is sent to the control unit wired or wirelessly.

In a twenty-first aspect of the present disclosure, which may be combined with the eighteenth aspect in combination with any other aspect listed herein unless specified otherwise, the PD system includes a network and at least one doctor or clinician computer in communication with the control unit via the network, the control unit configured to communicate the peritonitis determination to at least one of a patient or caregiver via a user interface of the cycler or the at least one doctor or clinician computer via the network.

In a twenty-second aspect of the present disclosure, which may be combined with the eighteenth aspect in combination with any other aspect listed herein unless specified otherwise, the bio-MEMS device is placed in fluid communication with a sample port of the disposable cassette.

In a twenty-third aspect of the present disclosure, which may be combined with the eighteenth aspect in combination with any other aspect listed herein unless specified otherwise, the bio-MEMS device includes a control unit having at least one of electronics, processing and memory, wherein either the cycler control unit or the bio-MEMS device control unit is configured to analyze the sensed temperature.

In a twenty-fourth aspect of the present disclosure, which may be combined with the eighteenth aspect in combination with any other aspect listed herein unless specified otherwise, the bio-MEMS device includes (i) a microfluidic chip forming a microfluidic pathway sized and configured to split the white blood cells from a remainder of effluent fluid and (ii) a piezoelectric biosensor that resonates with a frequency proportional to a property of the collected white blood cells.

In a twenty-fifth aspect of the present disclosure, which may be combined with the twenty-fourth aspect in combination with any other aspect listed herein unless specified otherwise, the property of the collected white blood cells includes a change in the deposition rate of the white blood cells.

In a twenty-sixth aspect of the present disclosure, which may be combined with the twenty-fourth aspect in combination with any other aspect listed herein unless specified otherwise, the frequency proportional to a property of the collected white blood cells is used to form the peritonitis determination.

In a twenty-seventh aspect of the present disclosure, which may be combined with the twenty-fourth aspect in combination with any other aspect listed herein unless specified otherwise, the piezoelectric biosensor operates with a collection area for collecting the white blood cells.

In a twenty-eighth aspect of the present disclosure, which may be combined with the eighteenth aspect in combination with any other aspect listed herein unless specified otherwise, the bio-MEMS device is in wired communication with the control unit or includes a wireless module for wireless communication with the control unit.

In a twenty-ninth aspect of the present disclosure, which may be combined with the eighteenth aspect in combination with any other aspect listed herein unless specified otherwise, the PD system is configured to analyze an amount of white blood cells removed from the effluent PD fluid to make the peritonitis determination.

In a thirtieth aspect of the present disclosure, which may be combined with the eighteenth aspect in combination with any other aspect listed herein unless specified otherwise, the peritonitis determination is a first peritonitis indicator, and which includes at least one different peritonitis indicator useable in combination with the first peritonitis indicator to form an overall peritonitis determination.

In a thirty-first aspect of the present disclosure, which may be combined with the thirtieth aspect in combination with any other aspect listed herein unless specified otherwise, the at least one different peritonitis indicator useable in combination with the first peritonitis indicator is obtained from at least one of a patient effluent PD fluid temperature sensor or a white blood cell impedance sensor.

In a thirty-second aspect of the present disclosure, which may be combined with the eighteenth aspect in combination with any other aspect listed herein unless specified otherwise, the peritonitis determination is provided in combination with insulin injection made using feedback from a patient effluent glucose biosensor.

In a thirty-third aspect of the present disclosure, which may be combined with any other aspect listed herein unless specified otherwise, a peritoneal dialysis ("PD") system includes: a cycler having a pump actuator and a control unit in operable communication with the pump actuator; a disposable set including a disposable cassette having a pump chamber, the disposable cassette sized and arranged to be held by the cycler such that the pump chamber is in operable communication with the pump actuator, the disposable set including a patient line and a drain line extending from the disposable cassette; a catheter for placement within a patient's peritoneal cavity and for fluid communication with the patient line; and an impedance sensor operably coupled to one of the catheter, patient line, or drain line to sense an impedance of PD fluid residing within the patient, or removed from the patient, the sensed impedance used to detect white blood cells to form a patient peritonitis determination, the control unit configured to communicate the peritonitis determination.

In a thirty-fourth aspect of the present disclosure, which may be combined with the thirty-third aspect in combination with any other aspect listed herein unless specified otherwise, the sensed impedance is sent to the control unit, and wherein the control unit is configured to analyze the sensed impedance.

In a thirty-fifth aspect of the present disclosure, which may be combined with the thirty-fourth aspect in combination with any other aspect listed herein unless specified otherwise, the sensed impedance is sent to the control unit wired or wirelessly.

In a thirty-sixth aspect of the present disclosure, which may be combined with the thirty-third aspect in combination with any other aspect listed herein unless specified otherwise, the PD system includes a network and at least one doctor or clinician computer in communication with the control unit via the network, the control unit configured to communicate the peritonitis determination to at least one of a patient or caregiver via a user interface of the cycler or the at least one doctor or clinician computer via the network.

In a thirty-seventh aspect of the present disclosure, which may be combined with the thirty-third aspect in combination with any other aspect listed herein unless specified otherwise, the PD system includes a water purifier configured to supply purified water to the disposable set, the water purifier including a water purifier control unit, wherein the sensed impedance is sent to the water purifier control unit, wherein the water purifier control unit is configured to analyze the sensed impedance, and wherein the cycler control unit and the water purifier control unit are in communication to allow the cycler control unit to communicate the peritonitis determination.

In a thirty-eighth aspect of the present disclosure, which may be combined with the thirty-third aspect in combination with any other aspect listed herein unless specified otherwise, the impedance sensor is located within a connector configured to couple to the catheter, the patient line or the drain line.

In a thirty-ninth aspect of the present disclosure, which may be combined with the thirty-eighth aspect in combination with any other aspect listed herein unless specified otherwise, the connector is (i) a clamshell connector that fits around the catheter, the patient line or the drain line or (ii) configured to be spliced between two sections of the catheter, the patient line or the drain line.

In a fortieth aspect of the present disclosure, which may be combined with the thirty-third aspect in combination with any other aspect listed herein unless specified otherwise, the impedance sensor includes electrodes positioned and arranged within the catheter, the patient line or the drain line, the connector positioned over the electrodes.

In a forty-first aspect of the present disclosure, which may be combined with the fortieth aspect in combination with any other aspect listed herein unless specified otherwise, the connector includes leads extending from the electrodes to (i) the control unit, (ii) a control unit of a water purifier configured to supply purified water to the disposable set, or (iii) a wireless module provided with the connector.

In a forty-second aspect of the present disclosure, which may be combined with the thirty-third aspect in combination with any other aspect listed herein unless specified otherwise, the PD system is configured to analyze the sensed impedance of the PD fluid residing within the patient, or removed from the patient, via a frequency sweep that moves from a start frequency to a stop frequency.

In a forty-third aspect of the present disclosure, which may be combined with the forty-second aspect in combination with any other aspect listed herein unless specified otherwise, the frequency sweep is generated by a frequency generator provided by or operable with the control unit.

In a forty-fourth aspect of the present disclosure, which may be combined with the forty-second aspect in combination with any other aspect listed herein unless specified otherwise, the PD system is configured to take an impedance measurement at two or more frequencies of the frequency sweep.

In a forty-fifth aspect of the present disclosure, which may be combined with the forty-second aspect in combination with any other aspect listed herein unless specified otherwise, the frequency sweep enables fluid having white blood cells and residing within the patient, or removed from the patient, to be determined by measuring, over at least a portion of the frequency sweep, higher impedances for the fluid having white blood cells than impedances for fluid not having white blood cells. And, the measured impedances for fluid not having white blood cells (i) are determined based on standard impedances or (ii) are determined based on impedances established for the patient.

In a forty-sixth aspect of the present disclosure, which may be combined with the forty-second aspect in combination with any other aspect listed herein unless specified otherwise, the frequency sweep enables fluid having white blood cells and residing within the patient, or removed from the patient, to be distinguished from fluid having fibrin, wherein the fluid having fibrin yields higher impedances over at least a portion of the sweep than the fluid having white blood cells.

In a forty-seventh aspect of the present disclosure, which may be combined with the thirty-third aspect in combination with any other aspect listed herein unless specified otherwise, the peritonitis determination is a first peritonitis indicator, and which includes at least one different peritonitis indicator useable in combination with the first peritonitis indicator to form an overall peritonitis determination.

In a forty-eighth aspect of the present disclosure, which may be combined with the forty-seventh aspect in combination with any other aspect listed herein unless specified otherwise, the at least one different peritonitis indicator useable in combination with the first peritonitis indicator is obtained from at least one of a patient effluent PD fluid temperature sensor or a white blood cell biosensor.

In a forty-ninth aspect of the present disclosure, which may be combined with the thirty-third aspect in combination with any other aspect listed herein unless specified otherwise, the peritonitis determination is provided in combination with insulin injection made using feedback from a patient effluent glucose biosensor.

In a fiftieth aspect of the present disclosure, which may be combined with the thirty-third aspect in combination with any other aspect listed herein unless specified otherwise, a peritoneal dialysis ("PD") system includes: a cycler including a pump actuator and a control unit in operable communication with the pump actuator; a disposable set including a disposable cassette having a pump chamber, the disposable cassette sized and arranged to be held by the cycler such that the pump chamber is in operable communication with the pump actuator; an insulin source in fluid communication with the disposable set; and a micro-electro-mechanical-system ("MEMS") affinity glucose sensor positioned and arranged to receive effluent PD fluid removed from a patient, the MEMS affinity glucose sensor configured to provide a glucose assessment concerning glucose absorbed by a patient, the glucose assessment used to determine an insulin dose, and wherein the control unit is configured to deliver the insulin dose from the insulin source to the patient via the pump actuator operating with the pump chamber of the disposable cassette.

In a fifty-first aspect of the present disclosure, which may be combined with the fiftieth aspect in combination with any other aspect listed herein unless specified otherwise, the PD system includes a dialysis fluid source in fluid communication with the disposable set, and wherein the control unit is configured to deliver the insulin dose from the insulin source to the patient mixed with fresh dialysis fluid from the dialysis fluid source.

In a fifty-second aspect of the present disclosure, which may be combined with the fifty-first aspect in combination with any other aspect listed herein unless specified otherwise, the dialysis fluid source is a point of use dialysis fluid source, wherein the fresh dialysis fluid is mixed within a mixing bag along with insulin from the insulin bag.

In a fifty-third aspect of the present disclosure, which may be combined with the fiftieth aspect in combination with any other aspect listed herein unless specified otherwise, the disposable set includes a patient line and a drain line in fluid communication with the disposable cassette, the MEMS affinity glucose sensor in fluid communication with the drain line.

In a fifty-fourth aspect of the present disclosure, which may be combined with the fifty-third aspect in combination with any other aspect listed herein unless specified otherwise, the MEMS affinity glucose sensor is located along the drain line upstream of a drain container.

In a fifty-fifth aspect of the present disclosure, which may be combined with the fiftieth aspect in combination with any other aspect listed herein unless specified otherwise, the PD system includes a water purifier, wherein the dialysis fluid source is a point of use dialysis fluid source using purified water from the water purifier, and wherein the MEMS affinity glucose sensor is provided with the water purifier.

In a fifty-sixth aspect of the present disclosure, which may be combined with the fifty-fifth aspect in combination with any other aspect listed herein unless specified otherwise, the water purifier is in wired or wireless communication with the cycler, wherein the water purifier is configured to determine the insulin dose from the glucose assessment and deliver the insulin dose to the cycler for delivery.

In a fifty-seventh aspect of the present disclosure, which may be combined with the fiftieth aspect in combination with any other aspect listed herein unless specified otherwise, the MEMS affinity glucose sensor is in wired or wireless communication with the cycler, wherein the control unit of the cycler is configured to determine the insulin dose from the glucose assessment sent from the MEMS affinity glucose sensor to the control unit.

In a fifty-eighth aspect of the present disclosure, which may be combined with the fiftieth aspect in combination with any other aspect listed herein unless specified otherwise, the MEMS affinity glucose sensor is configured to determine the insulin dose from the glucose assessment.

In a fifty-ninth aspect of the present disclosure, which may be combined with the fiftieth aspect in combination with any other aspect listed herein unless specified otherwise, the glucose assessment is indicative of an amount or concentration of glucose absorbed by the patient.

In a sixtieth aspect of the present disclosure, which may be combined with the fiftieth aspect in combination with any other aspect listed herein unless specified otherwise, the MEMS affinity glucose sensor includes (i) a microfluidic chip forming a microfluidic pathway sized and configured to split glucose molecules from a remainder of effluent fluid and (ii) a piezoelectric biosensor that resonates with a frequency proportional to a property of the collected glucose molecules.

In a sixty-first aspect of the present disclosure, which may be combined with the sixtieth aspect in combination with any other aspect listed herein unless specified otherwise, the property of the collected glucose molecules includes a change in the deposition rate of the glucose molecules.

In a sixty-second aspect of the present disclosure, which may be combined with the sixtieth aspect in combination with any other aspect listed herein unless specified otherwise, the frequency proportional to a property of the collected glucose molecules is used to form the insulin determination.

In a sixty-third aspect of the present disclosure, which may be combined with the sixtieth aspect in combination with any other aspect listed herein unless specified otherwise, the piezoelectric biosensor operates with a collection area for collecting the glucose molecules.

In a sixty-fourth aspect of the present disclosure, which may be combined with the fiftieth aspect in combination with any other aspect listed herein unless specified otherwise, the control unit is programmed assuming the lower the concentration of glucose in the effluent, the higher the amount of glucose absorbed by the patient.

In a sixty-fifth aspect of the present disclosure, which may be combined with the fiftieth aspect in combination with any other aspect listed herein unless specified otherwise, the PD system includes a network and at least one doctor or clinician computer in communication with the control unit via the network, the control unit configured to communicate the insulin dose to at least one of a patient or caregiver via a user interface of the cycler or the at least one doctor or clinician computer via the network.

In a sixty-sixth aspect of the present disclosure, which may be combined with the fiftieth aspect in combination with any other aspect listed herein unless specified otherwise, the PD system includes at least one peritonitis indicating device selected from a patient effluent PD fluid temperature sensor, a white blood cell biosensor or a white blood cell impedance monitor.

In a sixty-seventh aspect of the present disclosure, which may be combined with any other aspect listed herein unless specified otherwise, a peritoneal dialysis ("PD") system includes: a cycler including a pump actuator and a control unit in operable communication with the pump actuator; a disposable set including a pump portion sized and arranged to be held by the cycler such that the pump portion is in operable communication with the pump actuator, the disposable set including a patient line and a drain line extending from the disposable cassette; a catheter for placement within a patient's peritoneal cavity and for fluid communication with the patient line; and an impedance sensor operably coupled to one of the catheter, patient line, or drain line to sense an impedance of PD fluid residing within the patient, or removed from the patient, the sensed impedance used to detect white blood cells to form a patient peritonitis determination.

In a sixty-eighth aspect of the present disclosure, which may be combined with any other aspect listed herein unless specified otherwise, a peritoneal dialysis ("PD") system includes: a pump actuator and a control unit in operable communication with the pump actuator; a disposable set including a pump portion sized and arranged to be placed in operable communication with the pump actuator, the disposable set including a patient line and a drain line extending from the disposable cassette; a catheter for placement within a patient's peritoneal cavity and for fluid communication with the patient line; and an impedance sensor operably coupled to one of the catheter, patient line, or drain line to sense PD fluid residing within the patient, or removed from the patient, over a frequency sweep that moves from a start frequency to a stop frequency, the sensed impedance frequency sweep used to detect white blood cells to form a patient peritonitis determination.

In a sixty-ninth aspect of the present disclosure, any of the structure and functionality disclosed in connection with FIGS. 1 to 20B may be included or combined with any of the other structure and functionality disclosed in connection with FIGS. 1 to 20B.

In light of the present disclosure and the above aspects, it is therefore an advantage of the present disclosure to provide an improved peritoneal dialysis ("PD") system and method.

It is another advantage of the present disclosure to provide a PD system and method that enable peritonitis to be determined on an objective basis.

It is a further advantage of the present disclosure to provide a PD system and method that enable peritonitis to be determined automatically without over-burdening the patient.

It is still another advantage of the present disclosure to provide a PD system and method that enable peritonitis to be determined using multiple different procedures that provide cross-checking.

It is still a further advantage of the present disclosure to provide a PD system and method that proportion insulin infusion with dialysis fluid infusion at a desired concentration.

It is yet another advantage of the present disclosure to provide a PD system and method that communicate relevant peritonitis and insulin infusion data remotely to a clinician.

The advantages discussed herein may be found in one, or some, and perhaps not all of the embodiments disclosed herein. Additional features and advantages are described herein, and will be apparent from, the following Detailed Description and the figures.

BRIEF DESCRIPTION OF THE FIGURES

FIG. 3 is a front elevation view of one embodiment of a temperature sensing connector of the present disclosure.

FIGS. 4A and 4B are front elevation and perspective views, respectively, of another embodiment of a temperature sensing connector of the present disclosure.

FIG. 5 is a side elevation view of a further embodiment of a temperature sensing connector of the present disclosure.

FIG. 6 is a schematic view of one embodiment of a wirelessly operated temperature sensing connector of the present disclosure.

FIGS. 7A and 7B are schematic plots showing outputs of various temperature sensing connectors of the present disclosure.

FIGS. 8A and 8B are schematic plots showing outputs of other temperature sensing connectors of the present disclosure.

DETAILED DESCRIPTION

System Overview

The feedback systems and methods described herein are applicable with peritoneal dialysis ("PD"). The feedback systems and methods are mainly applicable to automated peritoneal dialysis ("APD"), which involves the use of a PD machine or cycler. It should be appreciated however that feedback systems and methods are also applicable to continuous ambulatory peritoneal dialysis ("CAPD"). With CAPD, the feedback systems and methods are implemented in stand alone devices that read out to the patient and/or communicate data remotely to a caregiver database for review by a doctor or clinician. Regarding APD machines, suitable cyclers include, e.g., the Amia® or HomeChoice® cycler marketed by Baxter International Inc. For example, the Amia® cycler is disclosed in U.S. Pat. No. 9,981,079, while the HomeChoice® cycler is disclosed in U.S. Pat. No. 5,350,357, the contents of each of which are incorporated by reference and relied upon. The above-incorporated patents each disclose the use of pre-packaged, pre-sterilized container or bags of PD dialysis fluid. The feedback systems and methods are applicable and implementable with cyclers using pre-packaged, pre-sterilized PD fluid. As discussed below, the feedback systems and methods are also applicable and implementable with cyclers using PD fluid made online or at the point of use.

Figure 1:
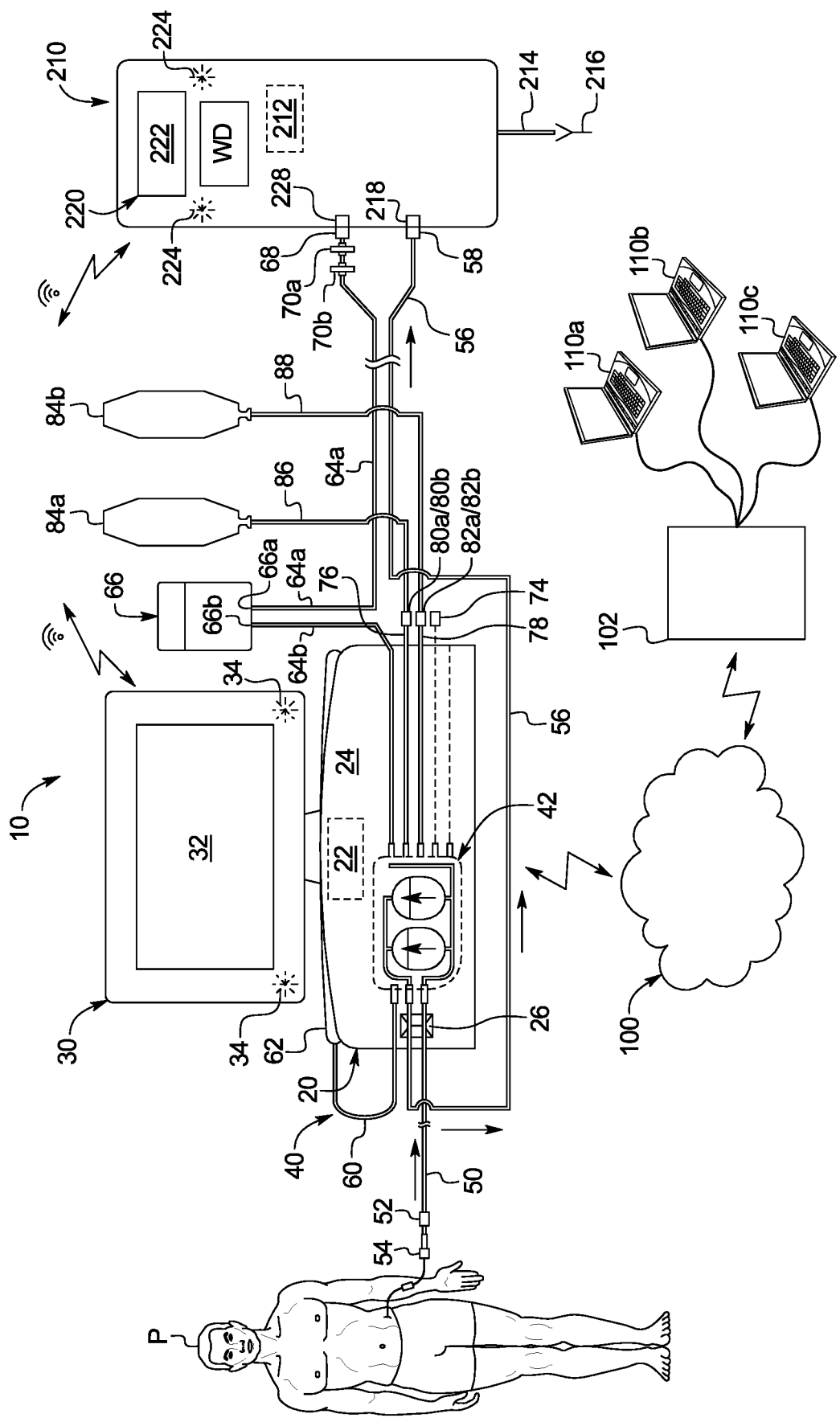
FIG. 1 is a front elevation view of one embodiment of a peritoneal dialysis delivery system having point of use dialysis fluid production, which communicates with a remote doctor or clinician data collection regime.

Referring now to FIG. 1, one embodiment of a peritoneal dialysis system having point of use dialysis fluid production is illustrated by system 10. System 10 includes a cycler 20 and a water purifier 210. Suitable cyclers for cycler 20 include, e.g., the Amia® or HomeChoice® cycler as mentioned above, with the understanding that those cyclers are provided with updated programming to perform and use the point of use dialysis fluid produced according to system 10. To this end, cycler 20 includes a control unit 22 having at least one processor and at least one memory. Control unit 22 further includes a wired or wireless transceiver for sending information to and receiving information from a water purifier 210 and other wireless devices discussed herein. Water purifier 210 also includes a control unit 212 having at least one processor and at least one memory. Control unit 212 further includes a wired or wireless transceiver for sending information to and receiving information from control unit 22 of cycler 20 and other wireless devices discussed herein. Wired communication may be via Ethernet connection, for example. Wireless communication may be performed via any of Bluetooth™, WiFi™, Zigbee®, Z-Wave®, wireless Universal Serial Bus ("USB"), or infrared protocols, or via any other suitable wireless communication technology.

Cycler 20 includes a housing 24, which holds equipment programmed via control unit 22 to prepare fresh dialysis solution at the point of use, pump the freshly prepared dialysis fluid to patient P, allow the dialysis fluid to dwell within patient P, then pump used dialysis fluid to a drain. In the illustrated embodiment, water purifier 210 includes a drain line 214 leading to a drain 216, which can be a house drain or a drain container. The equipment programmed via control unit 22 to prepare fresh dialysis solution at the point of use in an embodiment includes equipment for a pneumatic pumping system, including but not limited to (i) one or more positive pressure reservoir, (ii) one or more negative pressure reservoir, (iii) a compressor and a vacuum pump each under control of control unit 22, or a single pump creating both positive and negative pressure under control of control unit 22, to provide positive and negative pressure to be stored at the one or more positive and negative pressure reservoirs, (iv) plural pneumatic valve chambers for delivering positive and negative pressure to plural fluid valve chambers, (v) plural pneumatic pump chambers for delivering positive and negative pressure to plural fluid pump chambers, (vi) plural electrically actuated on/off pneumatic solenoid valves under control of control unit 22 located between the plural pneumatic valve chambers and the plural fluid valve chambers, (vii) plural electrically actuated variable orifice pneumatic valves under control of control unit 22 located between the plural pneumatic pump chambers and the plural fluid pump chambers, (viii) a heater under control of control unit 22 for heating the dialysis fluid as it is being mixed in one embodiment, and (ix) an occluder 26 under control of control unit 22 for closing the patient and drain lines in alarm and other situations.

In one embodiment, the plural pneumatic valve chambers and the plural pneumatic pump chambers are located on a front face or surface of housing 24 of cycler 20. The heater is located inside housing 24 and in an embodiment includes heating coils that contact a heating pan or tray, which is located at the top of housing 24, beneath a heating lid (not seen in FIG. 1).

Cycler 20 in the illustrated embodiment includes a user interface 30. Control unit 22 in an embodiment includes a video controller, which may have its own processing and memory for interacting with primary control processing and memory of control unit 22. User interface 30 includes a video monitor 32, which may operate with a touch screen overlay placed onto video monitor 32 for inputting commands via user interface 30 into control unit 22. User interface 30 may also include one or more electromechanical input device, such as a membrane switch or other button. Control unit 22 may further include an audio controller for playing sound files, such as voice activation commands, at one or more speaker 34.

Water purifier 210 in the illustrated embodiment also includes a user interface 220. Control unit 212 of water purifier 210 in an embodiment includes a video controller, which may have its own processing and memory for interacting with primary control processing and memory of control unit 212. User interface 220 includes a video monitor 222, which may likewise operate with a touch screen overlay placed onto video monitor 222 for inputting commands into control unit 212. User interface 220 may also include one or more electromechanical input device, such as a membrane switch or other button. Control unit 212 may further include an audio controller for playing sound files, such as alarm or alert sounds, at one or more speaker 224 of water purifier 210.

Figure 2:
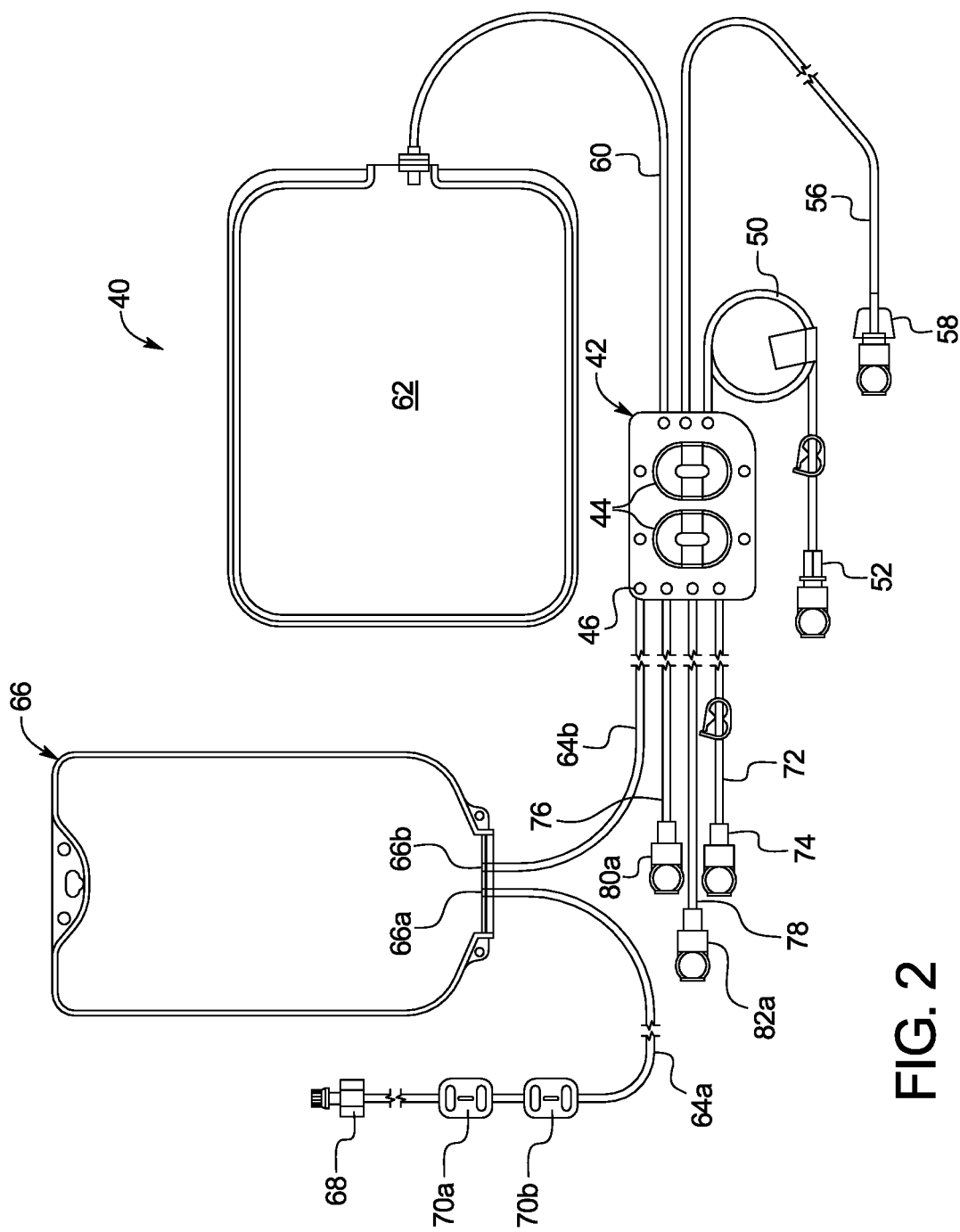
FIG. 2 is a top plan view of one embodiment of a disposable set used with the system illustrated in FIG. 1.

Referring additionally to FIG. 2, one embodiment of disposable set 40 is illustrated. Disposable set 40 is also illustrated in FIG. 1, mated to cycler 20 to move fluid within the disposable set 40, e.g., to mix dialysis fluid as discussed herein. Disposable set 40 in the illustrated embodiment includes a disposable cassette 42, which may include a planar rigid plastic piece covered on one or both sides by a flexible membrane. The membrane pressed against housing 24 of cycler 20 forms a pumping and valving membrane. FIG. 2 illustrates that disposable cassette 42 includes fluid pump chambers 44 that operate with the pneumatic pump chambers located at housing 24 of cycler 20 and fluid valve chambers 46 that operate with the pneumatic valve chambers located at housing 24 of cycler 20.

FIGS. 1 and 2 illustrate that disposable set 40 includes a patient line 50 that extends from a patient line port of cassette 42 and terminates at a patient line connector 52. FIG. 1 illustrates that patient line connector 52 connects to a patient transfer set 54, which in turn connects to an indwelling catheter located in the peritoneal cavity of patient P (see FIG. 11). Disposable set 40 includes a drain line 56 that extends from a drain line port of cassette 42 and terminates at a drain line connector 58. FIG. 1 illustrates that drain line connector 58 connects removeably to a drain connector 218 of water purifier 210.

FIGS. 1 and 2 further illustrate that disposable set 40 includes a heater/mixing line 60 that extends from a heater/mixing line port of cassette 42 and terminates at a heater/mixing bag 62 discussed in more detail below. Disposable set 40 includes an upstream water line segment 64a that extends to a water inlet 66a of water accumulator 66. A downstream water line segment 64b extends from a water outlet 66b of water accumulator 66 to cassette 42. In the illustrated embodiment, upstream water line segment 64a begins at a water line connector 68 and is located upstream from water accumulator 66. FIG. 1 illustrates that water line connector 68 is removeably connected to a water outlet connector 228 of water purifier 210.

Water purifier 210 outputs water and possibly water suitable for peritoneal dialysis ("WFPD"). To ensure WFPD, however, a sterilizing grade filter 70a is placed upstream from a downstream sterilizing grade filter 70b, respectively. Filters 70a and 70b may be placed in water line segment 64a upstream of water accumulator 66. Sterilizing grade filters 70a and 70b may be pass-through filters that do not have a reject line. Suitable sterilizing grade filters 70a and 70b may be provided by the assignee of the present disclosure. In an embodiment, only one of upstream or downstream sterilizing grade filter 70a and 70b is needed to produce WFPD, nevertheless, two sterilizing grade filters 70a and 70b are provided in the illustrated embodiment for redundancy in case one fails.

FIG. 2 further illustrates that a last bag or sample line 72 may be provided that extends from a last bag or sample port of cassette 42. Last bag or sample line 72 terminates at a connector 74, which may be connected to a mating connector of a premixed last fill bag of dialysis fluid or to a sample bag or other sample collecting container. Last bag or sample line 72 and connector 74 may be used alternatively for a third type of concentrate if desired.

FIGS. 1 and 2 illustrate that disposable set 40 includes a first, e.g., glucose, concentrate line 76 extending from a first concentrate port of cassette 42 and terminates at a first, e.g., glucose, cassette concentrate connector 80a. A second, e.g., buffer, concentrate line 78 extends from a second concentrate port of cassette 42 and terminates at a second, e.g., buffer, cassette concentrate connector 82a.

FIG. 1 illustrates that a first concentrate container 84a holds a first, e.g., glucose, concentrate, which is pumped from container 84a through a container line 86 to a first container concentrate connector 80b, which mates with first cassette concentrate connector 80a. A second concentrate container 84b holds a second, e.g., buffer, concentrate, which is pumped from container 84b through a container line 88 to a second container concentrate connector 82b, which mates with second cassette concentrate connector 82a.

In an embodiment, to begin treatment, patient P loads cassette 42 into cycler and in a random or designated order (i) places heater/mixing bag 62 onto cycler 20, (ii) connects upstream water line segment 64a to water outlet connector 228 of water purifier 210, (iii) connects drain line 56 to drain connector 218 of water purifier 210, (iv) connects first cassette concentrate connector 80a to first container concentrate connector 80b, and (v) connects second cassette concentrate connector 82a to second container concentrate connector 82b. At this point, patient connector 52 is still capped. Once fresh dialysis fluid is prepared and verified, patient line 50 is primed with fresh dialysis fluid, after which patient P may connect patient line connector 52 to transfer set 54 for treatment. Each of the above steps may be illustrated graphically at video monitor 32 and/or be provided via voice guidance from speakers 34.

For disposable set 40, the rigid portion of cassette 42 may be made for example of a medically acceptable rigid plastic. The flexible membranes of cassette 42 may be made for example of medically acceptable rigid plastic sheeting. Any of the bags or containers, such as heater/mixing bag or container 62 discussed below, may be made of medically acceptable plastic sheeting.

Control unit 22 may be programmed to cause cycler 20 to perform one or more mixing action to help mix dialysis fluid properly and homogeneously for treatment. For example, any of fluid pump chambers 44 may be caused to withdraw into the pump chambers some amount of mixed fluid (e.g., made from one or both first and second concentrates 84a, 84b and WFPD) from heater/mixing bag 62 and send such mixture back to heater/mixing bag 62 and repeat this procedure multiple times (described herein as a mixing sequence or "waffling"). In particular, to perform a mixing sequence, control unit 22 in an embodiment causes cycler 20 to close all fluid valve chambers 46 at cassette 42 except for the fluid valve chamber 46 to heater/mixing line 60 and heater/mixing bag 62. Fluid pump chambers 44 are stroked sequentially and repeatedly (i) pulling a possibly unmixed fluid combination of WFPD and concentrates from heater/mixing bag 62 into the pump chambers, followed by (ii) pushing the mixed WFPD and concentrates from the pump chambers back to heater/mixing bag 62 and (iii) repeating (i) and (ii) at least one time. Control unit 22 may be programmed to stroke fluid pump chambers 44 together so that they both pull and push at the same time, or alternatingly so that one pump chamber 44 pulls from heater/mixing bag 62, while the other pump chamber 44 pushes to heater/mixing bag 62, creating turbulence in heater/mixing line 60.

The configuration of container or bag 62 operable with cassette 42 and heater/mixing line 60 as illustrated in FIGS. 1 and 2 enables the WFPD from accumulator 66 and concentrates from first and second concentrate containers 84a and 84b to at least partially mix before entering the container or bag. Also, even if cassette 42 is not provided, the WFPD and at least one concentrate will mix partially in heater/mixing line 60 prior to reaching the container or bag.

FIG. 1 also illustrates that system 10 in one embodiment communicates via a network 100 with one or more caregiver server 102, which in turn is placed in operable communication with one or more doctor or clinician computer 110 to 110c. In the illustrated embodiment, network 100 is a cloud network, e.g., using one or more wide area network ("WAN"), such as an internet. Network 100 may alternatively be a more local area network ("LAN"). In the illustrated embodiment, cycler 20 of system 10 communicates with network 100 wirelessly via any of the protocols listed herein. In an alternative embodiment, cycler 20 of system 10 communicates with network 100 in a wired manner, e.g., using an Ethernet connection. In the illustrated embodiment, cycler 20 of system 10 communicates with network 100. In an alternative embodiment, water purifier 210 communicates alternatively or additionally with network 100 in a wireless or wired manner. In the illustrated embodiment, one or more caregiver server 102 communicates with network 100 wirelessly via any of the protocols listed herein. In an alternative embodiment, one or more caregiver server 102 communicates with network 100 in a wired manner, e.g., using an Ethernet connection. In the illustrated embodiment, doctor or clinician computers 110 to 110c communicate with one or more caregiver server 102 in a wired manner, e.g., using Ethernet connections. In an alternative embodiment, doctor or clinician computers 110 to 110c communicate with one or more caregiver server 102 wirelessly via any of the protocols listed herein.

Temperature Sensing for Peritonitis

Referring now to FIGS. 3 to 8B, in one primary embodiment, the temperature of used dialysis fluid exiting the patient is measured to detect peritonitis. In healthy patients, the temperature of used dialysis fluid is normal body temperature or about 37° C. In patients experiencing the onset of peritonitis, the used dialysis fluid exiting the patient may reside at an elevated temperature. The system and method of the first embodiment measure the effluent dialysis fluid and use the measurement to make a determination as to whether the patient may be experiencing the onset of peritonitis.

The temperature measurement may be made in a number of different ways. Temperature sensing connector 120 in FIG. 3 illustrates one mechanism for reading the temperature of the effluent fluid removed from patient P (FIG. 1). Connector 120 includes a primary housing 122, which may be made of any suitable medical grade material, such as a medical grade plastic. In the illustrated embodiment, housing 122 is spliced into patient line 50 (FIG. 1). Housing 122 includes a first port 124 that sealingly accepts a first spliced end 50a of patient line 50. First port 124 may for example include or be a hose barb port or be sized to stretch first spliced end 50a as illustrated. First port 124 may alternatively be a luer connector connecting to a mating luer connector end 50a of patient line 50. Housing 122 includes a second port 126 that sealingly accepts a second spliced end 50b of patient line 50. Second port 126 may be a male port just like port 124 or be a female port as illustrated which sealingly accepts second spliced end 50b via a compression fitting (to do so second spliced end 50b may be fitted with an internal rigid hose barb to maintain their shape of spliced end 50b when placed under compression). Female port 126 enables electrical leads 128a and 128b to extend out of housing 122 in the event that electrical signals are delivered via wire to control unit 22 of cycler 10 (or control unit 212 of water purifier 210).

Electrical leads 128a and 128b extend to probes or electrodes 130a and 130b, respectively, which contact effluent fluid traveling through housing 122 and provide a temperature reading for the fluid. Leads 128a and 128b and electrodes 130a and 130b may be overmolded into or adhered to the inner cylindrical surface of housing 122. The temperature sensor of connector 120 may be for example a thermocouple or thermistor. In the illustrated embodiment, electrodes 130a and 130b are the sensing portion of a K-type (chromel-alumel) thermocouple, which generates a voltage that may be sensed and which is proportional to a temperature of the effluent fluid.

Connector 120 illustrates multiple ways in which the generated voltage may be analyzed (as alternatives so not all of the structure illustrated in FIG. 3 needs be provided with connector 120, just the structure used). In one embodiment, leads 128a and 128b carry the generated voltage back to control unit 22 of cycler 20 (or control unit 212 of water purifier 210), wherein the electronics and processing of the control unit process the temperature proportional voltage signal and determine if the resulting temperature indicates peritonitis or the onset thereof.

In another embodiment (indicated by dashed lines), leads 128a and 128b carry the generated voltage to a wireless module 132 located along the outside of housing 122. Wireless module 132 is powered by a battery 134, such as a long-lasting lithium battery, and includes electronics configured to convert the temperature proportional voltage to a wireless signal, which is sent wirelessly to control unit 22 of cycler 20 in one embodiment. Control unit 22 of cycler 20 processes the wireless version of the temperature proportional voltage signal and determines if the resulting temperature indicates peritonitis or the onset thereof.

FIG. 3 illustrates an embodiment in which the connector is spliced in between two tubing segments. FIGS. 4A and 4B illustrate an alternative embodiment in which a clamshell temperature connector 140 instead fits over a tubing segment, such as a portion of patient line 50. In the illustrated embodiment, clamshell temperature connector 140 first directly over and contacts the medical grade polymer or plastic of patient line 50. In an alternative embodiment, a more thermally conductive medical grade segment 150, such as a stainless steel segment, is spliced in between two polymer or plastic segments of patient line 50. The more thermally conductive medical grade segment 150 may help to achieve a more accurate temperature measurement.

FIGS. 4A and 4B illustrate that clamshell temperature connector 140 includes a housing 142 having clamshell halves 144 and 146, which are hinged together along a living hinge 148 in the illustrated embodiment. Housing 142 is made of any suitable material, such as a medical grade plastic. Housing 142 is sized to form fit over patient line 50/150 in the illustrated embodiment.

Connector 140 includes electrical leads 152a and 152b that extend to probes or electrodes 154a and 154b, respectively, which contact patient line 50/150 to provide a temperature of the effluent fluid flowing through the line. Leads 152a and 152b and electrodes 154a and 154b may be overmolded into or adhered to the inner cylindrical surface of respective clamshell halves 144 and 146. The temperature sensor of connector 140 may again be a thermocouple or thermistor. In the illustrated embodiment, electrodes 154a and 154b are the sensing portion of a K-type (chromel-alumel) thermocouple, which generates a voltage that may be sensed and which is indicative of a temperature of the effluent fluid.

Connector 140 illustrates multiple ways in which the generated voltage may be analyzed (as alternatives so not all structure illustrated in FIGS. 4A and 4B needs to be provided with connector 140, just the structure used). In one embodiment, leads 152a and 152b carry the generated voltage back to control unit 22 of cycler 20 (or control unit 212 of water purifier 210), wherein the electronics and processing of the control unit processes the temperature proportional voltage signal and determines if the resulting temperature indicates peritonitis or the onset thereof.

In another embodiment (indicated by dashed lines), leads 152a and 152b carry the generated voltage to wireless module 132 located along the outside of housing 142. Wireless module 132 is powered by a battery 134, such as a long-lasting lithium battery, and includes electronics configured to convert the temperature proportional voltage to a wireless signal, which is sent wirelessly to control unit 22 of cycler 20 in one embodiment. Control unit 22 of cycler 20 processes the wireless version of the temperature proportional voltage signal and determines if the resulting temperature indicates peritonitis or the onset thereof.

FIG. 5 illustrates a further alternative embodiment in which a snap-fit temperature connector 160 is fitted to a wall of housing 24 of cycler 20 (or a wall of water purifier 210), either inside of outside of the machine. Snap-fit temperature connector 160 includes a housing 162, which is bolted to, adhered to, or formed by housing 24. Housing 162 is made of any suitable material, such as a medical grade plastic. Housing 162 includes a snap-fitting collar 164, which in combination with probes or electrodes 166a and 166b are sized to snap-fit over patient line 50/150 in the illustrated embodiment. The C-shaped collar 164 spreads apart slightly to accept patient line 50/150 and then spreads apart slightly again to release patient line 50/150 once treatment is completed.

Electrodes 166a and 166b may be overmolded into or adhered to the inner cylindrical surface of C-shaped collar 164. The temperature sensor of connector 160 may again be a thermocouple or thermistor. In the illustrated embodiment, electrodes 166a and 166b are the sensing portion of a K-type (chromel-alumel) thermocouple, which generates a voltage that may be sensed and which is indicative of a temperature of the effluent fluid. In the illustrated embodiment, electrodes 166a and 166b extend respectively to leads 168a and 168b, which carry the generated voltage through the wall of housing 24 and to control unit 22 of cycler 20 (or control unit 212 of water purifier 210), wherein the electronics and processing of the control unit processes the temperature proportional voltage signal and determines if the resulting temperature indicates peritonitis or the onset thereof.

FIG. 6 illustrates schematically the wireless version of the temperature sensing of the first primary embodiment. Patient line 50 or thermally conductive patient line segment 150 carries effluent fluid. Electrodes E (representing all electrodes discussed above) contact the outer wall of patient line 50 or thermally conductive patient line segment 150 as illustrated or contact the effluent fluid directly (FIG. 3). A temperature indicating voltage is carried via leads L (representing all leads discussed above) to wireless module 132. Wireless module 132 is powered by a battery 134, such as a long-lasting lithium battery, and incldues electronics configured to convert the temperature proportional voltage to a wireless signal, which is sent wirelessly to a desired control unit.

FIG. 6 also illustrates another alternative embodiment in which electrodes E are located instead along the sheeting of disposable cassette disposable cassette 42. Here, the electrodes E are located inside cycler 20 and are aligned automatically with cassette 42 when the cassette is installed. The patient or caregiver is not required to take any additional action. In this scenario, wireless module 132 is not needed and leads L run instead directly to control unit 22.

As discussed above, testing the temperature of the effluent fluid of patient P is used to determine if the patient has peritonitis. The effluent fluid flows from patient P, though patient transfer set 54, patient line connector 52, patient line 50, disposable set 40, drain line 56, drain line connector 58, and drain connector 218 of water purifier 210. It is contemplated to place temperature sensing connectors 120, 140 or 160 at any of those locations, including as part of patient transfer set 54, patient line connector 52 or drain line connector 58. In one aspect, it is advantageous to place temperature sensing connectors 120, 140 or 160 as close to patient P as possible, e.g., at patient transfer set 54 or patient line connector 52, so as to sense as accurate a patient effluent temperature as possible. As shown below however, temperature sensing may be useful for the present purpose even if the true patient temperature is not sensed. Locating the temperature sensing for peritonitis along the drain line within water purifier 210 is advantageous if for example a temperature sensor already exists there for another purpose, such as to work in combination with a conductivity sensor to test the conductivity of dialysis fluid to determine mixing accuracy.

FIGS. 7A and 7B illustrate example data from either a direct fluid sensing embodiment (e.g., connector 120 of FIG. 3) or sensing through a thermally conductive patient tube segment 150 embodiment, each of which should read true fluid temperature. FIGS. 7A and 7B each show temperature reading for two fill phases (Fi1 and Fi2) and two drain phases (Dr1 and Dr2). Each fill phase is followed by a dwell period indicated by parallel lines. Each drain phase is followed by the next fill phase as indicated by a single vertical line.

Cycler 20 heats fresh dialysis fluid in heater/mixing bag 62 to body temperature or 37° C. prior to delivery via cassette 42 and patient line 50 to patient P. In each fill phase instance in FIGS. 7A and 7B, the temperature reading is at or about 37° C. as heated fresh fluid flows past the temperature sensor. The drain phase readings (Dr1 and Dr2) are the readings of effluent dialysis fluid from patient P, wherein the effluent fluid has resided within the patient for a prolonged period of time, e.g., at least one hour, such that the effluent fluid temperature provides a true indication of the patient's internal body temperature. FIG. 7A shows effluent temperature readings from a healthy PD patient, in which the readings may be at or slightly above body temperature or 37° C. FIG. 7B shows effluent temperature readings from a PD patient who may be experiencing peritonitis or the onset thereof, in which the readings are noticeably above body temperature, around 38° C. in the illustrated example.

It is contemplated to program temperature signal manipulation in evaluating the temperature readings. For example, assume the setpoint for generating a peritonitis alert is 38° C. The relevant processing and memory evaluating the temperature readings may be programmed to average the temperature readings over the course of the drain flow of effluent fluid past the temperature sensor. In this manner, a short temperature spike to 38° C. does not trigger an alert or flag. It is also contemplated to look to temperature readings over multiple effluent drains (e.g., Dr1 and Dr2), and to average same prior to making a determination whether or not to generate a peritonitis alert. For example, an alert is generated in one embodiment at the end of a treatment including multiple effluent drains when the totality of effluent temperature readings indicates peritonitis or the onset thereof, e.g., 38° C. or higher.

FIGS. 8A and 8B illustrate example data from a sensing through a generally non-thermally conductive patient tube segment 50 embodiment, wherein the temperature read may be below the true fluid temperature. FIGS. 8A and 8B each show temperature readings for two fill phases (Fi1 and Fi2) and two drain phases (Dr1 and Dr2). Each fill phase is followed by a dwell period indicated by parallel lines. Each drain phase is followed by the next fill phase as indicated by a single vertical line.

Because it is known that cycler 20 heats fresh dialysis fluid in heater/mixing bag 62 to body temperature or 37° C. prior to delivery via cassette 42 and patient line 50 to patient P, the temperatures of the fill phases in FIGS. 8A and 8B provide an accurate indication of the temperature reading offset due to the generally non-thermally conductive nature of the tubing of patient line 50 (e.g., polyvinyl-chloride ("PVC")). In the illustrated example of FIGS. 8A and 8B, the temperature of the the heated fresh PD fluid reads 32° C. instead of what is known to be 37° C. The relevant control unit 22 or 212 thereby determines that the present offset for the present tubing under the present environmental conditions is 5° C. The relevant control unit is programmed to then expect the effluent fluid removed from a healthy patient P to have roughly the same temperature offset, namely, to be around 32° C. The relevant control unit is also programmed to determine that patient P may have peritonitis if the temperature of the effluent fluid removed from the patient is a predefined amount above the offsetted temperature of around 32° C.

In each fill phase instance in FIGS. 8A and 8B, the offsetted temperature reading through the generally thermally non-conductive patient line tubing 50 is at or about 32° C. as heated fresh fluid flows past the temperature sensor. The drain phase readings (Dr1 and Dr2) are again the readings of effluent dialysis fluid from patient P, wherein the effluent fluid has resided within the patient for a prolonged period of time, e.g., at least one hour, such that the effluent fluid temperature provides a true indication of the patient's internal body temperature. FIG. 8A shows effluent temperature readings from a healthy PD patient, in which the readings may be at or slightly above the expected offsetted temperature of 32° C. FIG. 8B however shows effluent temperature readings from a PD patient who may be experiencing peritonitis or the onset thereof, in which the readings are noticeably above the expected offsetted temperature, around 34° C. in the illustrated example. For the expected offset example of FIGS. 8A and 8B, it is again contemplated to program the above-described temperature signal manipulation, e.g., averaging and accumulating over multiple fills and drains, in evaluating the temperature readings.

In the examples of FIGS. 7A to 8B, when the relevant control unit 22 or 212 determines that patient P may be experiencing peritonitis or the onset thereof, the control unit in one embodiment causes user interface 30 and/or 220 to provide an audio, visual or audiovisual alert to the patient and/or caregiver at cycler 20 and/or water purifier 210 of system 10. In one embodiment, even if the control unit evaluating the temperature readings for the peritonitis determination is control unit 212 of water purifier 210, the audio, visual or audiovisual alert is nevertheless provided at user interface 30 of cycler 20 by way of a wired or wireless communication from control unit 212 of water purifier 210 to control unit 22 of cycler 20 informing of the alert condition. In this manner, user interface 30 is the primary communication vehicle for a given treatment and patient P, and wherein user interface 220 is relegated to displaying water purifier related information.

In addition or perhaps alternatively to the alert provided to patient P or caregiver at user interface 30 of cycler 20, control unit 22 (or perhaps control unit 212) operates via network 100 and one or more caregiver server computer 102 to enable a doctor or clinician at one or more clinician computer 110a to 110c to receive and view effluent temperature data, e.g., on an ongoing basis, so that the doctor or clinician may determine if the patient has or is at risk of developing peritonitis. The data is displayed on clinician computer 110a to 110c in one embodiment via a dashboard of a website for the patient, wherein the temperature data may be presented with a flag for the clinician when it is elevated, indicating peritonitis.

It is contemplated to send effluent temperature data for patient P after every treatment regardless of whether the data indicates peritonitis. In this way, the doctor or clinician is able to develop a pattern or profile of effluent temperatures for the patient. It is contemplated that the website develops a graph or trend of effluent temperatures that are plotted against treatment dates, which is displayed upon request, for example, in addition to the dashboard. The trend as well as the dashboard in one embodiment pinpoints or flags temperature entries that may indicate peritonitis or the onset thereof. A doctor or clinician viewing multiple flagged peritonitis days is therefore able to determine with reasonable certainty that the patient needs treatment.

Bio-MEMS Sensing for Peritonitis

Figure 9:
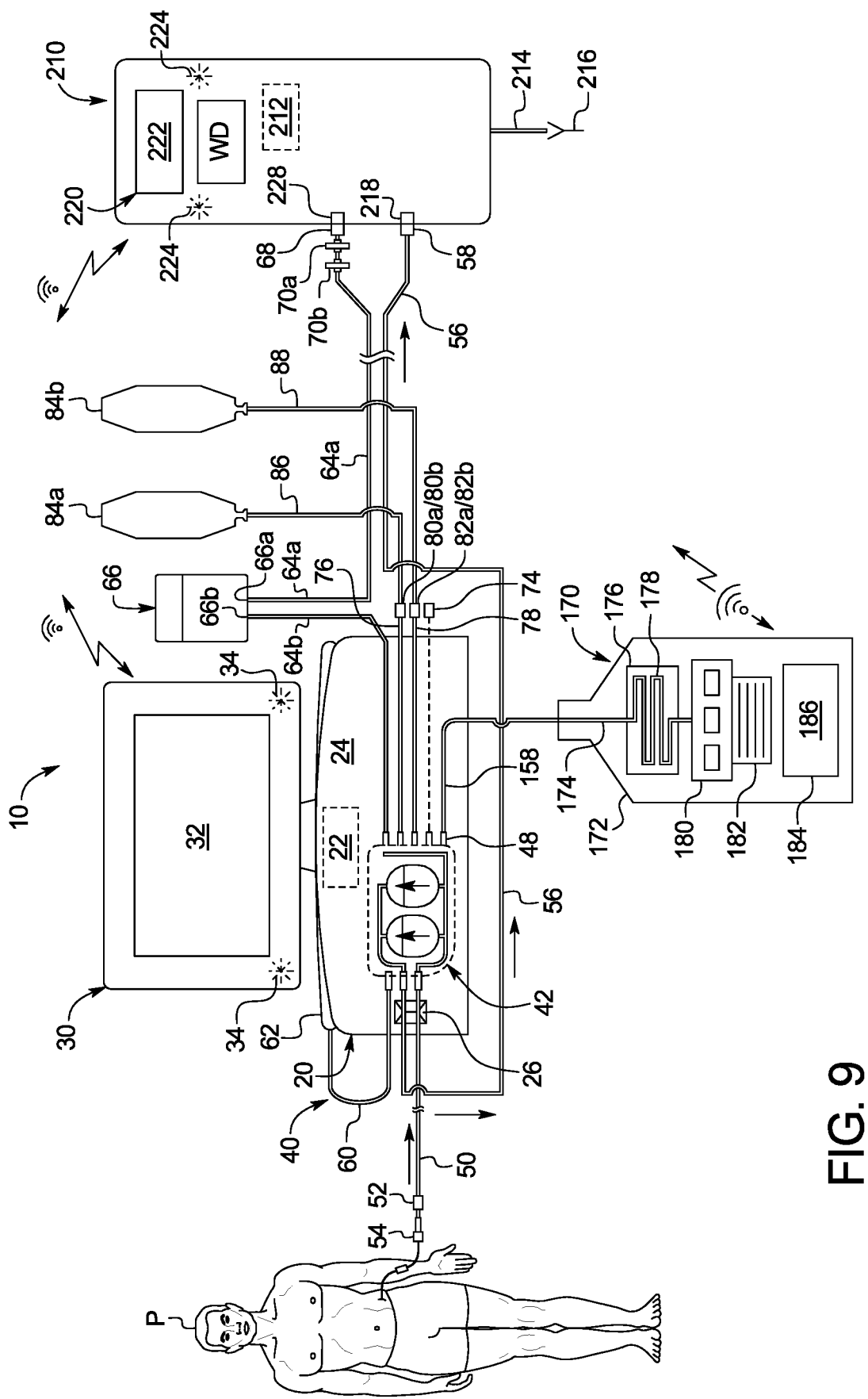
FIG. 9 is a front elevation view of a medical fluid delivery system having point of use dialysis fluid production, which operates with one embodiment of a white blood cell sensing device of the present disclosure.
Figure 10:
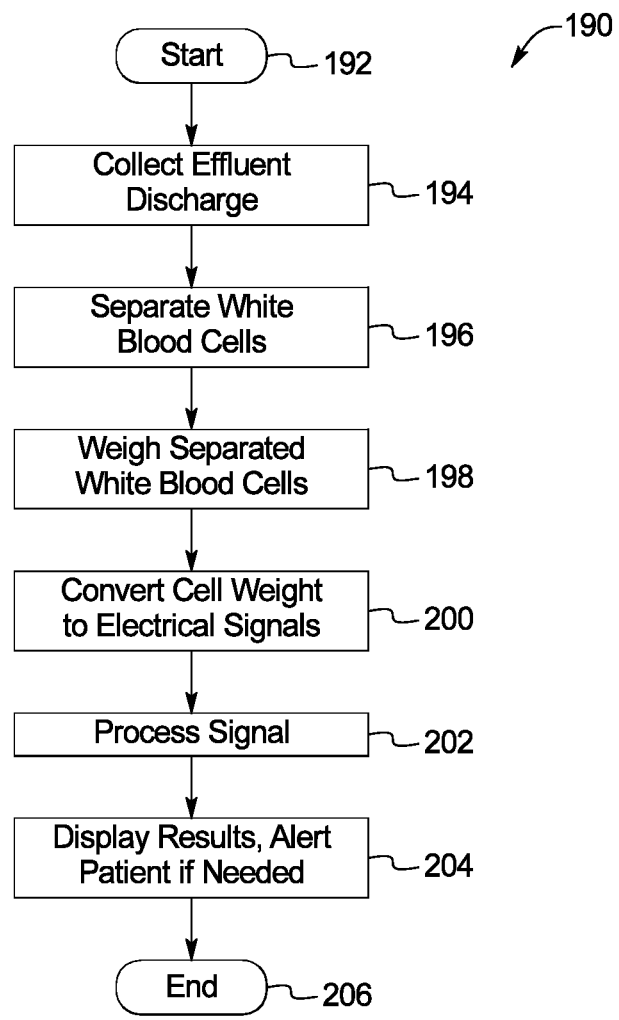
FIG. 10 is a schematic flow diagram of one embodiment of a white blood cell sensing method useable with the system of FIG. 9.

Referring now to FIGS. 9 and 10, in a second primary embodiment, a bio-Micro-Electro-Mechanical-System ("bio-MEMS") sensor is used to detect peritonitis. The bio-MEMS sensor is used to look for the presence of white blood cells from the patient in the effluent fluid, which is an indicator of peritonitis. FIG. 9 illustrates that in one implementation, effluent fluid from patient P is pumped via patient line 50 to cassette 42 loaded into cycler 20 and pumped thereafter from cassette 42 via drain line 56 to a drain at water purifier 210. Drain line 56 is connected to a lab-on-chip diagnostic detection or bio-MEMS device 170 in one embodiment. In the illustrated embodiment of FIG. 9 however an alternative is shown in which effluent fluid is pumped selectively via an extra sample port 48 and a sample line 158 to lab-on-chip diagnostic detection device 170. Using sample port 48 enables control unit 22 of cycler 20 to selectably deliver a desired amount of effluent fluid from patient P to lab-on-chip diagnostic detection device 170 at a desired time and/or frequency.

As illustrated in FIG. 9, lab-on-chip or bio-MEMS device 170 includes a container 172 to which a sampling line 158 extends and connects (e.g., via compression fitting, threaded fitting, luer connection, hose barb connection and combinations thereof) to an inlet line 174 located within container 172. Container 172 may be made of a medically acceptable metal or polymer, such as stainless steel or plastic such as PVC.

The effluent sample travels along inlet line 174 of bio-MEMS device 170 to a microfluidic pathway 178 formed on or in a microfluidic chip 176. Microfluidic chip 176 in various embodiments is made from inorganic materials, polymeric materials or paper. In various embodiments, microfluidic chip 176 is made of silicon, glass, polymer substrates, composites or paper. Microfluidic pathway 178 is sized and configured to split the patient's white blood cells from the remainder of effluent fluid.

The split off white blood cells are then delivered to a collection area 180 (made of the same material as container 172 or microfluidic chip 176 in various embodiments) where they are weighed or otherwise quantified by a piezoelectric biosensor 182. Piezoelectric sensor 182 in various embodiments uses a piezoelectric effect to measure a change in pressure, strain, or force due to the collected white blood cells by converting the changes to an electrical charge. In an embodiment, piezoelectric biosensor 182 resonates with a frequency proportional to a change in the deposition rate of white blood cells.

In the illustrated embodiment, bio-MEMS device 170 includes a control unit 184 having electronics, processing and memory to convert the frequency of resonation from biosensor 182 into a quantified amount representing the amount of white blood cells removed from the patient's effluent sample. Control unit 184 may also include a user interface 186 that displays an audio, visual or audiovisual message to the patient or caregiver indicating the presence or not of white blood cells and thus the presence or not of peritonitis or the onset thereof.

Alternatively, bio-MEMS device 170 includes electronics configured to convert the white blood cell quantity proportional voltage to a wireless signal as illustrated in FIG. 9, which is sent wirelessly to control unit 22 of cycler 20 in one embodiment. Here, user interface 186 is not needed and user interface 30 of cycler 20 is used instead. Processing and memory for device 170 may also not be needed.

Method 190 of FIG. 10 summarizes the methodology just described. At oval 192, method 190 begins. At block 194, patient P's effluent discharge is collected, e.g., via separate sample port 48 of cassette 42 and sample line 158 discussed above. At block 196, white blood cells if present are separated from the patient's effluent fluid, e.g., via microfluidic chip 176. At block 198, the separated white blood cells are weighed or otherwise quantified, e.g., via piezoelectric biosensor 182. At block 200, the white blood cell weight is converted into an electrical signal, e.g., via piezoelectric biosensor 182. At block 202, the electrical signal is processed into a form that may be used by control unit 22 (of cycler 20) or control unit 184 (of bio-MEMS device 170) to determine if the amount of white blood cells collected indicates peritonitis or the onset thereof. There may be an amount of white blood cells below which peritonitis is not presumed to be present. At block 204, the results of the white blood cell analysis are displayed at user interface 30 (of cycler 20) or user interface 186 (of bio-MEMS device 170) and the patient or caregiver is alerted if needed. At oval 206, method 206 ends.

While network 100, one or more caregiver server computer 102 and one or more clinician computer 110*a* to 110*c* are not illustrated in FIG. 9, they still may be present. And, in addition or perhaps alternatively to the alert provided to patient P or caregiver at user interface 30 or user interface 186, control unit 22 operates via network 100 and one or more caregiver server computer 102 to enable a doctor or clinician at one or more clinician computer 110*a* to 110*c* to receive and view effluent white blood cell collection data, e.g., on an ongoing basis, so that the doctor or clinician may determine if the patient has or is at risk of developing peritonitis. The data is displayed on clinician computer 110*a* to 110*c* in one embodiment via a dashboard of a website for the patient, wherein the effluent white blood cell collection data may be presented with a flag for the clinician when it is elevated, indicating peritonitis.

It is contemplated to send effluent white blood cell collection data for patient P after every treatment regardless of whether the data indicates peritonitis. In this way, the doctor or clinician is able to develop a pattern or profile of effluent white blood cell collection data for the patient. It is also contemplated that the website develops a graph or trend of effluent white blood cell collection amounts that are plotted against treatment dates, which is displayed upon request, for example, in addition to the dashboard. The trend as well as the dashboard in one embodiment pinpoints or flags white blood cell collection entries that may indicate peritonitis or the onset thereof. A doctor or clinician viewing multiple flagged peritonitis days is therefore able to determine with reasonable certainty that the patient needs treatment. The white blood cell collection data of the second primary embodiment may be displayed alternatively to or in addition to the effluent temperature data of the first primary embodiment. Providing both blood white blood cell collection data and effluent temperature data enables the doctor or clinician to view and analyze multiple peritonitis indicators in order to make a medical determination for the patient.

In an alternative embodiment, bio-MEMS device 170 is located instead in patient line 50 via a sample line and is used to analyze effluent returning from patient P. In this manner, the bio-MEMS device may be used to sense fresh dialysis fluid delivered to the patient additionally if desired. Or, control unit 20 may be programmed to periodically send fresh dialysis fluid into bio-MEMS device 170 via sample port 48 of cassette 42 and sample line 158 to sample a desired property of the fresh dialysis fluid.

Impedance Monitoring for Peritonitis

Figure 11:
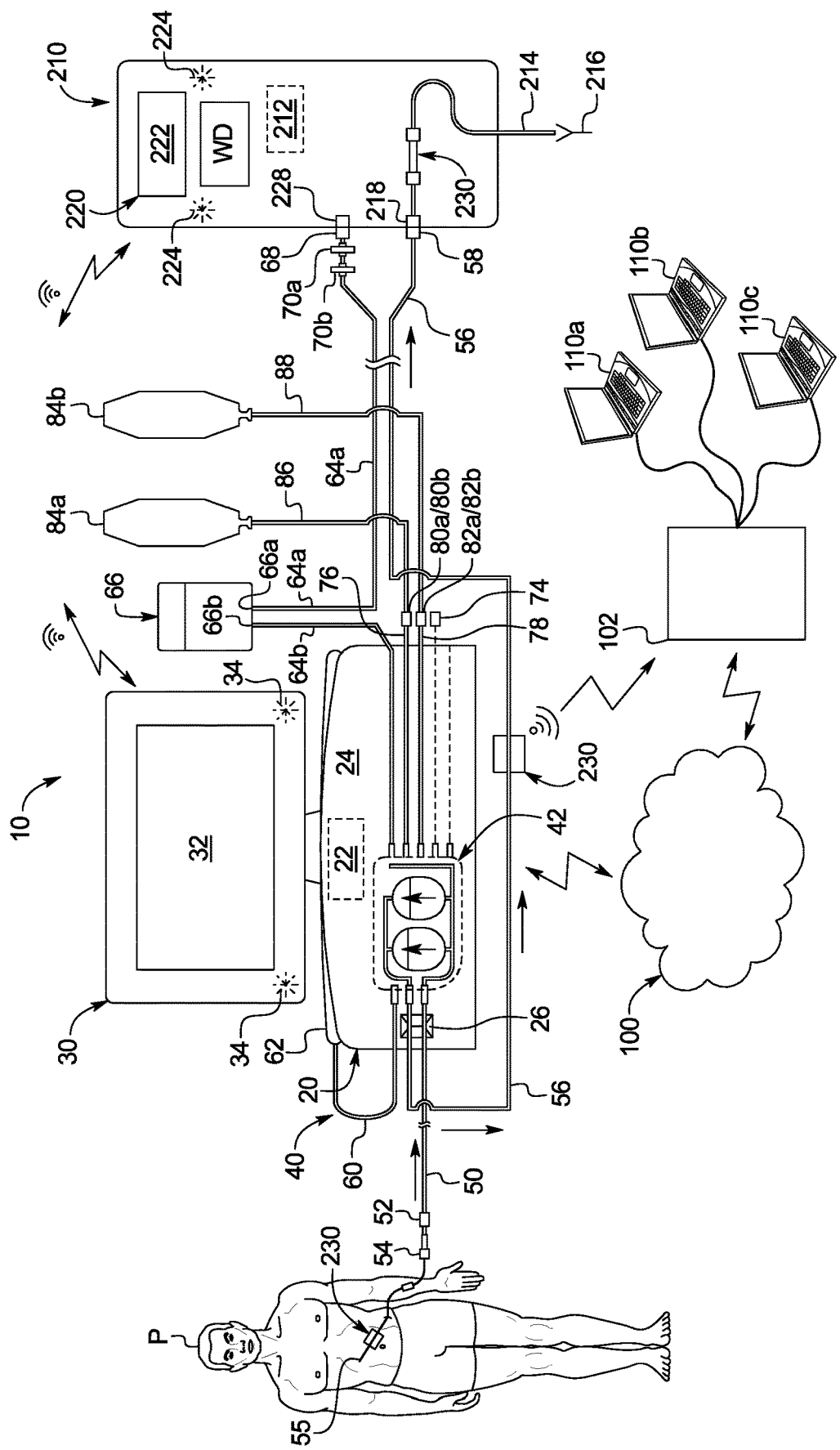
FIG. 11 is a front elevation view of a medical fluid delivery system having point of use dialysis fluid production, which operates with one embodiment of an effluent fluid impedance evaluation device of the present disclosure.
Figure 12:
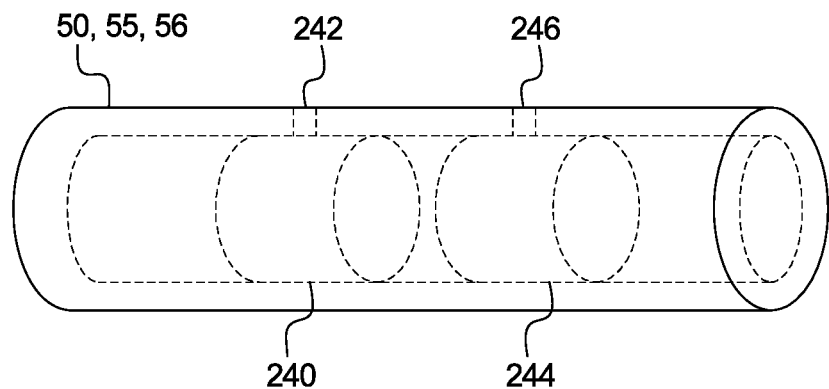
FIG. 12 is a front isometric view of one embodiment for electrode placement within a catheter or tube operating with an effluent fluid impedance evaluation device of the present disclosure.
Figure 13:
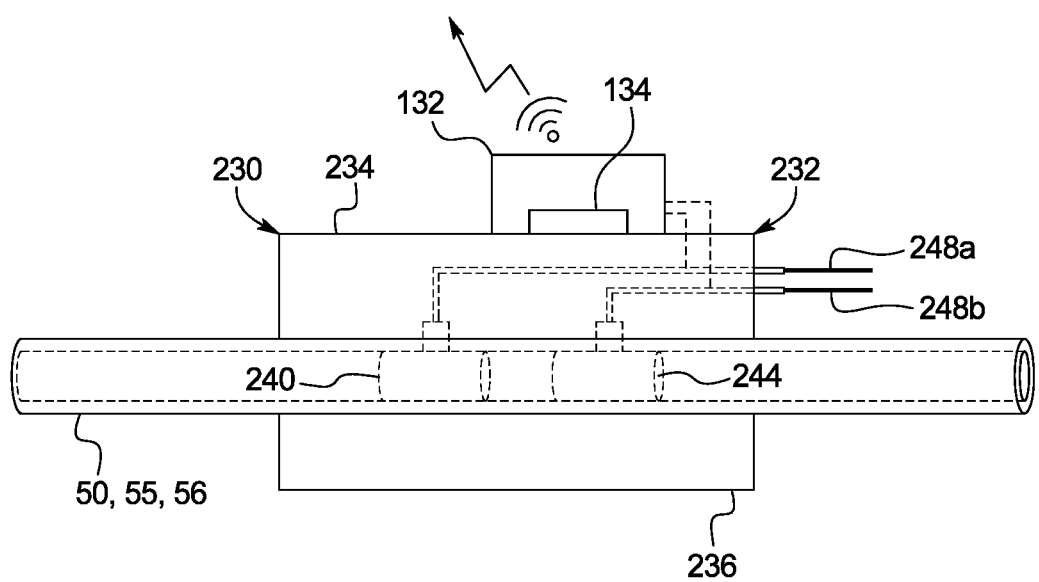
FIG. 13 is a front elevation view of one embodiment for a catheter impedance effluent evaluation device of the present disclosure.

Referring now to FIGS. 11 to 13, in a third primary embodiment, an impedance monitor is used to detect peritonitis. The impedance monitor is used to look for the presence of white blood cells from the patient in the effluent fluid, which again is an indicator of peritonitis. In various implementations, the impedance monitor may be placed anywhere that the patient's effluent fluid may be sensed, for example, in the patient's indwelling catheter, in the patient line or anywhere in the drain line. In any of these locations, the catheter or line is fitted with electrodes, e.g., in any of the ways discussed above for temperature sensing, but with the goal now of placing electrically conductive contacts in communication with the effluent dialysis fluid for impedance detection.

FIG. 11 illustrates an impedance monitor 230 placed in multiple locations. In a first location, impedance monitor 230 is placed along the indwelling catheter 55 of patient P, which is connected to patient transfer set 54 and is in fluid communication with patient line 50. In a second location (not illustrated), impedance monitor 230 is placed along patient line 50. In a third location (not illustrated), impedance monitor 230 is fixed within cycler 20 and located so as to operate with disposable cassette 42 or a line (patient line or drain line) extending from disposable cassette 42. In a fifth location, impedance monitor 230 is located along drain line 56 between cycler 20 and water purifier 210. In a sixth location, impedance monitor 230 is fixed within water purifier and is located along the drain line extending within the water purifier. In any of the above locations, impedance monitor 230 is able to sense effluent fluid to detect peritonitis.

FIGS. 12 and 13 illustrate one embodiment for impedance monitor 230. FIG. 12 illustrates that in one embodiment cylindrical electrodes 240 and 244 are fitted within patient line 50, the patient's indwelling catheter 55 or drain line 56. Cylindrical electrodes 240 and 244 in the illustrated embodiment are tubular segments or sections which have an outer diameter slightly larger than the inner diameter of line 50, 56 or catheter 55, such that electrodes 240 and 244 are press-fitted at desired locations within line 50, 56 or catheter 55. Electrodes 240 and 244 are made of an electrically conductive and medically safe material, such as stainless steel, titanium and combinations and alloys thereof. Electrodes 240 and 244 in the illustrated embodiment each include a female port or socket 242 and 246, respectively, which is configured to receive and hold a lead extending from the ports.

FIG. 13 illustrates that female ports or sockets 242 and 246 in one embodiment extend through line 50, 56 or catheter 55 in such a way that the line or catheter wall seals around female ports or sockets 242 and 246. FIG. 12 illustrates ports or sockets extending alternatively so as to be at least substantially flush with the outside of line 50, 56 or catheter 55. In either embodiment, the outer diameter of ports or sockets 242 and 246 is larger than the hole produced in line 50, 56 or catheter 55, such that the tube or catheter material is forced to stretch around and seal to the ports. In a further alternative embodiment (not illustrated), ports or sockets 242 and 246 do not extend outwardly from cylindrical electrodes 240 and 244 and the leads are instead pierced through the line 50, 56 or catheter 55. Here, the line 50, 56 or catheter 55 helps to hold the leads in place.

FIG. 13 illustrates that electrically conductive leads 248a and 248b extend respectively from ports or sockets 242 and 246. As with the temperature sensing connectors of FIGS. 3 to 4B, conductive leads 248a and 248b of impedance monitor 230 in one embodiment extend to control unit 22 of cycler 20 (or control unit 212 of water purifier 210), wherein the electronics and processing of the control unit causes the signal generation and processing discussed below to be performed. In an alternative embodiment (indicated by dashed lines), leads 248a and 248b receive power from and/or carry a generated voltage to wireless module 132 located along the outside of a housing 232 of impedance monitor 230. Wireless module 132 is again powered by a battery 134, such as a long-lasting lithium battery, and includes electronics configured to convert the voltage into a wireless signal and vice versa, which is communicated wirelessly to control unit 22 of cycler 20 in one embodiment.

Housing 232 may have clamshell halves 234 and 236, which are hinged together along a living hinge discussed in connection with FIGS. 4A and 4B. Housing 232 is sized to form fit over patient line 50, catheter 55 or drain line 56 in the illustrated embodiment. Housing 232 is alternatively spliced between two segments of patient line 50, catheter 55 or drain line 56 in a manner the same as or similar to temperature sensing connector 120 in FIG. 3. Housing 232 in any of the above embodiments is made of any suitable material, such as a medical grade plastic.

Control unit 22 (of cycler 20) or control unit 212 (of water purifier 210) controlling impedance monitor 230 in one embodiment causes an electrical frequency sweep to be generated in the effluent fluid. The control unit may include or operate with a frequency sweep generator that moves from a start frequency to a stop frequency at a specified sweep rate. It is contemplated to sweep up or down in frequency, with either linear or logarithmic spacing. It is also contemplated to program the control unit to sweep sine, square, pulse, ramp, triangle, or arbitrary waveforms. It is further contemplated to specify a hold time, during which the sweep remains at the stop frequency, and a return time, during which the frequency changes linearly from the stop frequency to the start frequency.

As the impedance monitor 230 steps though the frequencies of the sweep, the resulting impedance of the effluent fluid in the indwelling catheter is measured at each different frequency. The impedances of the effluent fluid may be compared against those of fresh dialysis fluid to determine if a difference results. The impedance spectroscopy (or obtaining complex impedance) in one embodiment provides additional details about the content(s) of the effluent fluid. For example, the electrical properties of fibrin (normal, not indicating peritonitis) may vary from the electrical properties of white blood cells (indicating peritonitis). Once control unit 22 (of cycler 20) or control unit 212 (of water purifier 210) learns the electrical properties of different substances that may reside within the effluent fluid, the properties may be programmed into the control unit and used thereafter to determine what if anything is entrained in the effluent dialysate stream.

Figure 14A:
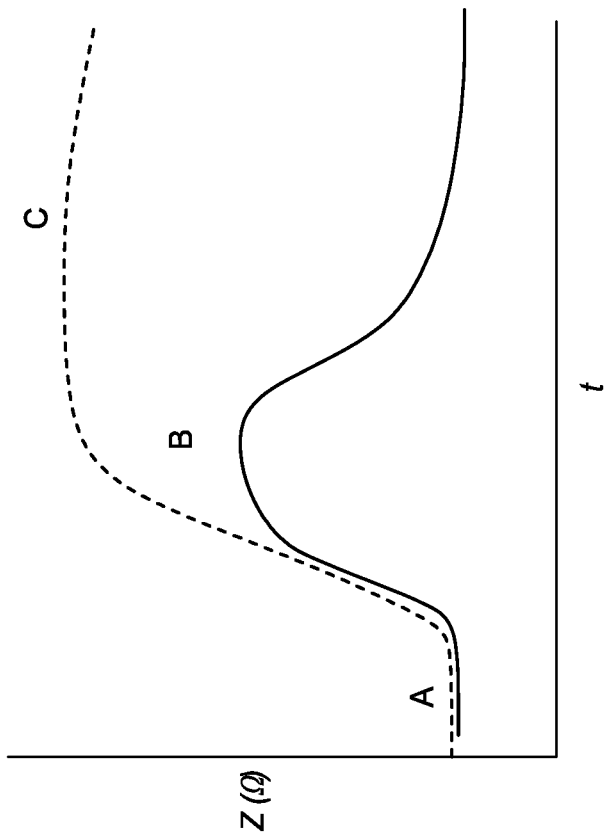
FIGS. 14A and 14B are schematic plots showing impedance outputs over time and over a frequency sweep, respectively, for normal patient effluent, patient effluent having white blood cells (indicating peritonitis) and patient effluent having fibrin.
Figure 14B:
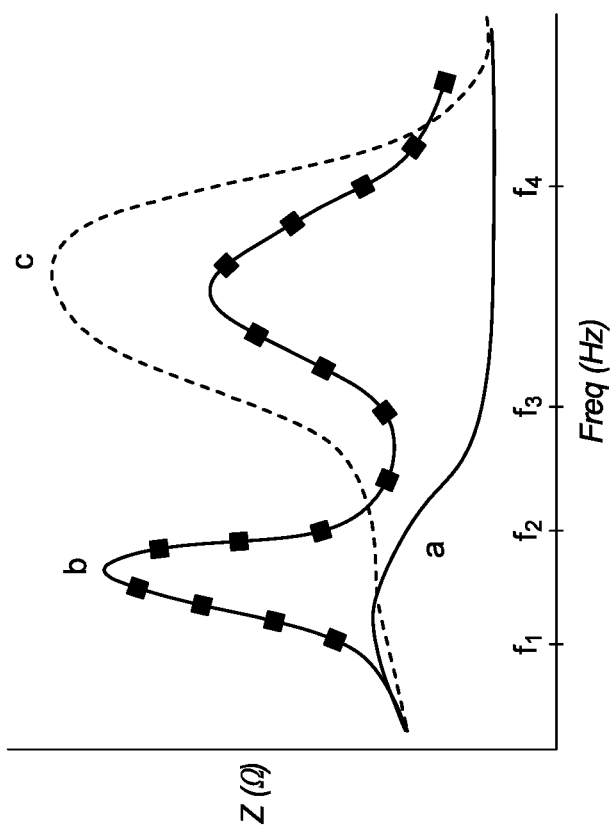

FIGS. 14A and 14B illustrate example plots of impedance (Z) measured in ohms (Ω) for normal patient effluent, patient effluent having white blood cells (indicating peritonitis), and patient effluent having other particulates, such as fibrin. FIG. 14A shows impedance measurements over time, which can be continuous or discrete (on command). The example time-based output shows continuous data of (A) normal effluent impedance (continuous line only) and (C) effluent with increased fibrin content (dashed line), e.g., over the course of a dwell phase of a patient's peritoneal dialysis treatment. In the illustrated example, the plots for impedance over time for effluent with normal fibrin (A) and effluent with increased fibrin (C) start out together but then the impedance for effluent with increased fibrin rises substantially above that of effluent with normal fibrin. It is expected that the curve for an episode of peritonitis would be represented by a line extending in the area marked (B), between that of effluent with normal fibrin (A) and effluent with increased fibrin (C), which is confirmed in FIG. 14B. FIG. 14B shows that as the patient's dwell phase proceeds, a clear difference between effluent with normal fibrin and effluent with increased fibrin emerges.

FIG. 14B illustrates of an impedance spectrogram corresponding to curves illustrated in the time-based plot of FIG. 14A. The example frequency-based output shows continuous data of (a) normal effluent impedance (continuous line only), (b) an episode of peritonitis resolved by antibiotics (continuous line with boxes), and (c) effluent with increased fibrin content (dashed line) the data at the points highlighted in the left frame. Spectrograms (a) to (c) cover a frequency range in one example of 10 Hz to $10^6$ Hz.

The example frequency-based output of FIG. 14B illustrates that there is likely to be one or more frequency range in which the impedance difference between effluent with white blood cells (b) and the normal effluent (a) is more starkly different than with other frequencies. In FIG. 14B, two such frequency ranges exist between $f_1$ and $f_2$ and between $f_3$ and $f_4$. Having multiple starkly different frequency ranges enables control unit 22 or 212 to cross-check the result of one of the ranges against that of the other. If both or all frequency ranges indicate peritonitis, then control unit 22 or 212 (or clinician computer 110a to 110c) outputs a determination that the patient has or is beginning to experience peritonitis to user interface 30, user interface 220, and/or to clinician computers 110a to 110c via network 100 and caregiver server computer 102. In another embodiment, control unit 22 or 212 integrates the area under impedance curve (b) and compares it to an integration of the area under impedance curve (a) to determine peritonitis or the onset thereof.

In one embodiment, curve (a) for normal effluent is determined empirically via testing on multiple patients and then averaged to develop standardized impedance values over the frequency sweep range. The standardized values in an embodiment are determined for each of the popular and most frequently use glucose level peritoneal dialysis fluids as impedance may vary based upon starting glucose levels. The standardized impedance values may be provided as a range that accounts for differing dwell times, differing effluent temperatures, and other factors.

In another embodiment, curve (a) for normal effluent is determined empirically, again, but here for the specific patient using system 10 and cycler 20. Impedance data is taken over multiple treatments or for all treatments. A normal effluent impedance average is formed, which may be a rolling average that may move or shift over time. It is determined that curve (b) for peritonitis effluent is present in one embodiment when the impedances in the relevant frequency ranges or averaged via integration are some predetermined percentage higher than the patient-specific curve (a).

Regarding increased fibrin content curve (c), FIG. 14B illustrates that there is one or more specific frequency range, here between $f_1$ and $f_2$, in which the impedance of effluent having white blood cells indicating peritonitis (b) is significantly higher than the impedance of effluent having increased fibrin (c). Thus, in FIG. 14B the most important range may be said to be between frequency range $f_1$ and $f_2$ because an increased impedance between frequency range $f_3$ and $f_4$ could be due either to effluent having white blood cells indicating peritonitis (b) or effluent having increased fibrin (c).

It is alternatively or additionally contemplated for control unit 22 or 212 (or clinician computer 110a to 110c) to look at the shape of the impedance curve over the frequency range. If the shape is closest to curve (a), control unit 22 or 212 (or clinician computer 110a to 110c) determines that the patient effluent is normal. If the shape is closest to curve (b), control unit 22 or 212 (or clinician computer 110a to 110c) determines that the patient effluent shows signs of peritonitis or the onset thereof. If the shape is closest to curve (c), control unit 22 or 212 (or clinician computer 110a to 110c) determines that the patient effluent has increased fibrin levels.

In any embodiment in which the impedance monitor 230 is located remote from cycler 20 or water purifier 210, the impedance monitor may send the measured signals in a wired or wireless manner to the cycler for interrogation. Impedance monitor 230 as mentioned above has the ability to emit a frequency sweep into the effluent fluid and thus may receive power either via battery 134 (in a wireless embodiment) or from the cycler or water purifier via power wires.

As discussed above, in an alternative embodiment, impedance monitor 230 is located within cycler 20 or water purifier 210. In such case, impedance monitor 230 emits the frequency sweep into the effluent fluid by receiving power from the cycler or water purifier via power wires. As mentioned above, impedance monitor 230 may operate with disposable cassette 42 loaded into cycler 20. Here, impedance monitor 230 may extend through a rigid wall holding the disposable cassette sheeting in one or more places.

Control unit 22 or 212 is programmed in one embodiment to alert the patient or caregiver at user interface 30 of cycler 20 if white blood cells indicating peritonitis are detected. In one embodiment, even if the control unit evaluating the impedance sweep readings for white blood cells is control unit 212 of water purifier 210, the audio, visual or audiovisual alert is nevertheless provided at user interface 30 of cycler 20 by way of a wired or wireless communication from control unit 212 of water purifier 210 to control unit 22 of cycler 20 informing of the alert condition. In this manner, user interface 30 is the primary communication vehicle for a given treatment and patient P, and wherein user interface 220 is relegated to displaying water purifier related information.

In addition or perhaps alternatively to the alert provided to patient P or caregiver at user interface 30, control unit 22 operates via network 100 and one or more caregiver server computer 102 to enable a doctor or clinician at one or more clinician computer 110a to 110c to receive and view the impedance obtained effluent white blood cell data, e.g., on an ongoing basis, so that the doctor or clinician may determine if the patient has or is at risk of developing peritonitis. The data is displayed on clinician computer 110a to 110c in one embodiment via a dashboard of a website for the patient, wherein the effluent white blood cell collection data may be presented with a flag for the clinician when it is elevated, indicating peritonitis.

It is contemplated to send the impedance obtained effluent white blood cell data for patient P after every treatment regardless of whether the data indicates peritonitis. In this way, the doctor or clinician is able to develop a pattern or profile of effluent white blood cell data for the patient. It is also contemplated that the website develops a graph or trend of effluent white blood cell amounts that are plotted against treatment dates, which is displayed upon request, for example, in addition to the dashboard. The trend as well as the dashboard in one embodiment pinpoints or flags white blood cell entries that may indicate peritonitis or the onset thereof. A doctor or clinician viewing multiple flagged peritonitis days is therefore able to determine with reasonable certainty that the patient needs treatment. The white blood cell data of the third primary embodiment may be displayed alternatively to or in addition with the white blood cell collection data of the second primary embodiment and/or the effluent temperature data of the first primary embodiment. Providing both white blood cell data embodiments and effluent temperature data enables the doctor or clinician to view and analyze multiple peritonitis indicators in order to make a medical determination for the patient.

Glucose Control for Diabetes Patients

Referring now to FIGS. 15 to 20B, in a fourth primary embodiment, system 10 provides a MEMS affinity glucose sensor 250, which matches or helps to match the amount of insulin provided to patient P with an amount of glucose delivered to the patient during treatment. FIG. 14 illustrates a version of system 10 which uses pre-prepared PD fluid in containers or bags 94a and 94b instead of making PD fluid online or at the point of use using glucose, concentrate 84a, buffer concentrate 84b, or purified water from a water purifier 210 and stored in an accumulator 66, which is shown in FIGS. 1, 9, 11 and 15. In either version however, patient P receives glucose from the PD fluid. That is, the pre-prepared PD fluid in container or bags 94a and 94b includes glucose, which is at a level prescribed by a doctor or clinician. It should be appreciated that any of the primary embodiments discussed herein may be provided instead using the pre-prepared PD fluid version of system 10 illustrated in FIG. 14.

Figure 15:
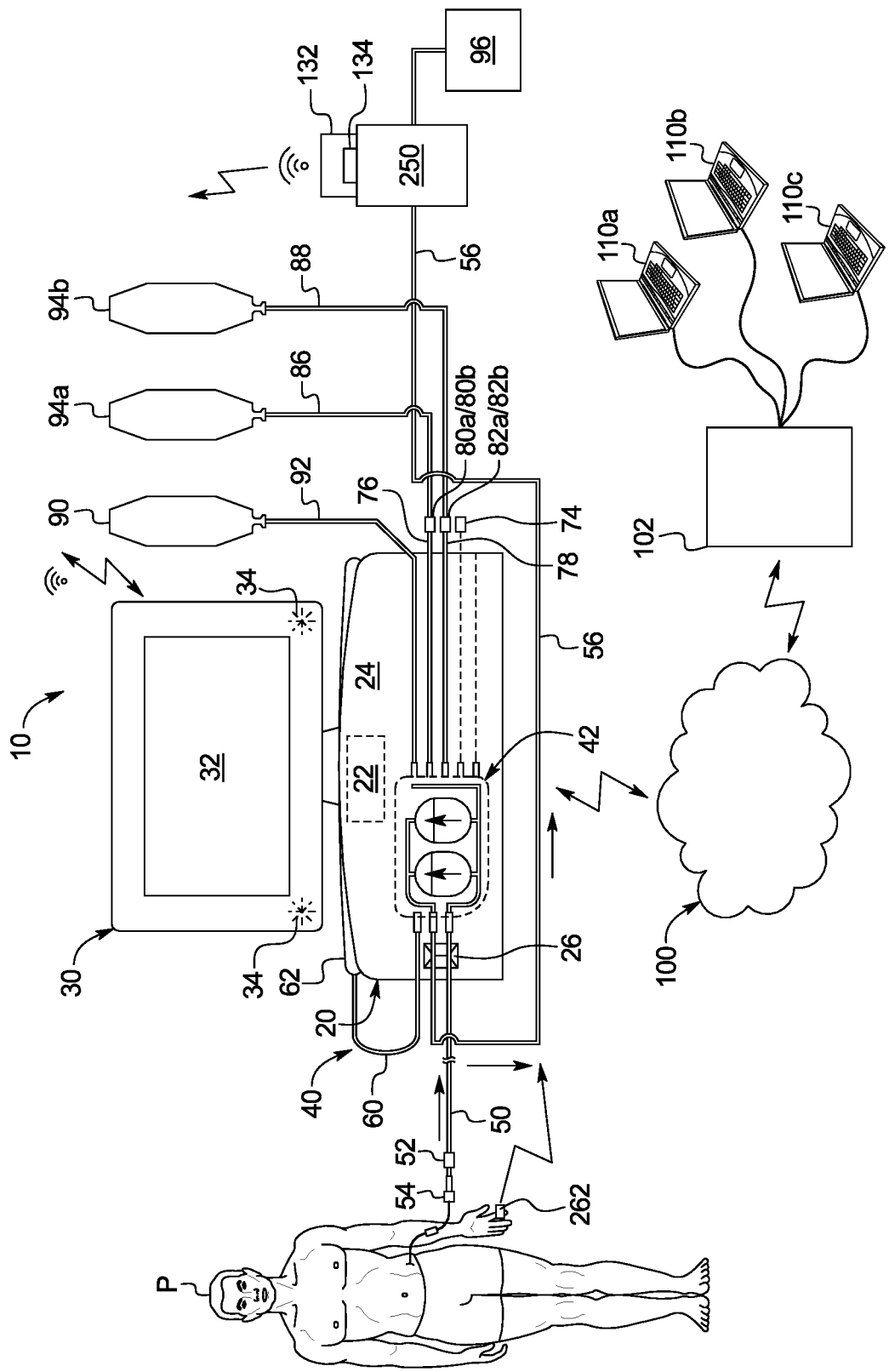
FIG. 15 is a front elevation view of a medical fluid delivery system operating with presterilized containers of peritoneal dialysis fluid, which further operates with one embodiment of an effluent glucose sensing and insulin controlling device of the present disclosure.

FIG. 15 illustrates that in one pre-prepared PD fluid embodiment, an insulin container or bag 90 is connected to the port of cassette 42 that connected to accumulator 66 in the point of use examples. A MEMS affinity glucose sensor 250 is provided in drain line 56 upstream of a drain bag 96. MEMS affinity glucose sensor 250 measures the glucose level of the effluent dialysis fluid leaving patient P via drain line 56.

Figure 16:
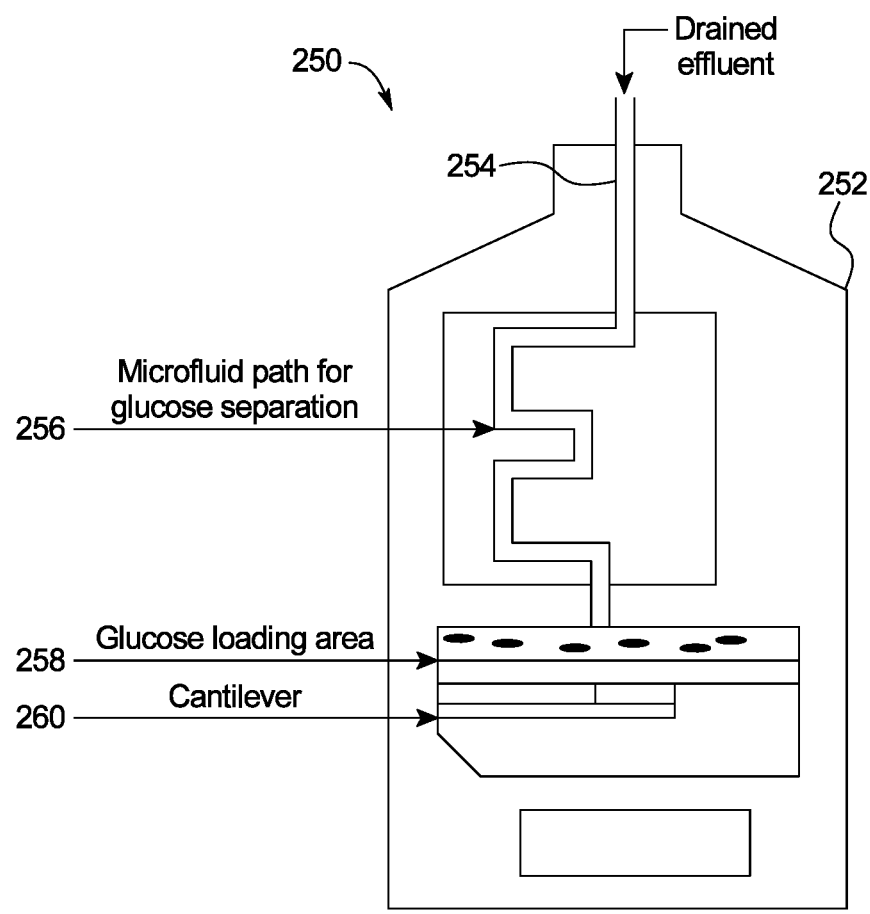
FIG. 16 is a front elevation view of one embodiment of a MEMS affinity glucose sensor useable with the systems of FIGS. 15 and 17.

FIG. 16 illustrates that in one embodiment, MEMS affinity glucose sensor 250 includes a container 252 into which a sampling line 254 extends, wherein sampling line 254 may extend or tee off of drain line 56. The effluent sample entering container 252 of MEMS affinity glucose sensor 250 first encounters a microfluidic pathway 256 that splits the glucose molecules from the effluent fluid. The glucose molecules are then weighed using a piezoelectric biosensor 258 in the illustrated embodiment. Piezoelectric biosensor 258 includes a cantilever 260 that resonates with a frequency proportional to a change in the deposition rate of glucose molecules. The relation between the resonant frequency to glucose found in the effluent fluid is illustrated below in connection with FIG. 18. Glucose absorbed at the end of an nth PD cycle is calculated using the equation for $A_n$ discussed below. To compensate for the absorbed glucose in the the nth PD cycle, the administration of the insulin dosage during the subsequent n+1 PD cycle is calculated using an equation for $I_{n+1}$ discussed below.

The MEMS affinity glucose sensor 250 in one embodiment includes the electronics and processing to process raw signals from piezoelectric biosensor 258 and to make a determination as to the proper concentration of insulin to prepare with the PD solution. MEMS affinity glucose sensor 250 may also include a user interface to indicate to the patient or caregiver present during treatment that the proper insulin level is being determined. In alternative embodiments, either one or both of (i) electronics and processing to process raw signals from piezoelectric biosensor 258 or (ii) the user interface for patient or caregiver communication are provided instead by the control unit of cycler 20 or water purifier 210 operable with the cycler.

MEMS affinity glucose sensor 250 in FIG. 15 includes wireless module 132 located along the outside of the housing of device 250. Wireless module 132 as discussed herein is powered by a battery 134, such as a long-lasting lithium battery, and includes electronics configured to convert the measured patient effluent glucose level into a wireless signal, which is sent wirelessly to control unit 22 of cycler 20 in one embodiment. Control unit 22 of cycler 20 processes the glucose level wireless signal and determines an amount of insulin from insulin container or bag 90 to deliver to heater bag 62 for the next patient PD fill. It should be noted that patient P is sometimes full of fluid from the previous treatment when beginning a current treatment.

The amount of insulin to deliver is based upon a desired insulin concentration, which is correlated to the amount of glucose sensed via sensor 250 and sent to control unit 22. Knowing the desired insulin concentration and the amount of fresh pre-prepared PD fluid from one of containers or bags 92a or 92b to be delivered to heater bag 62, the amount of insulin to deliver from container or bag 90 to heater bag 62 is determined and then pumped via fluid pump chambers 44 of disposable cassette 42 to heater bag 62. In an alternative embodiment, the amount of insulin is pumped instead from insulin container or bag 90 to pre-prepared PD fluid container or bag 92a or 92b via fluid pump chambers 44 of disposable cassette 42 or via a separate pump (not illustrated). An insulin port may be provided on pre-prepared PD fluid container or bags 92a and 92b to receive the insulin.

FIG. 15 also illustrates that system 10 using MEMS affinity glucose sensor 250 in one embodiment also includes a glucose sensor 262, which is applied, e.g., to a finger of patient P. Such glucose sensors are known in the art in either prick or non-prick forms. In the illustrated embodiment, glucose sensor 262 outputs a glucose reading wirelessly to control unit 22, control unit 212 or MEMS affinity glucose sensor 250. Wired communication between glucose sensor 262 and control unit 22, control unit 212 or MEMS affinity glucose sensor 250 is also possible. The reading(s) from glucose sensor 262 at the beginning of treatment is used in one embodiment discussed below to determine an amount of insulin to inject in a next PD fill cycle. Reading(s) from glucose sensor 262 may also be used at the end of treatment to confirm that the blood sugar level of patient P has remained within a safe band using the glucose feedback and insulin injection of the present disclosure. All such information may also be sent to clinician computers 110a to 110c via network 100 and one or more caregiver server computer 102.

Figure 17:
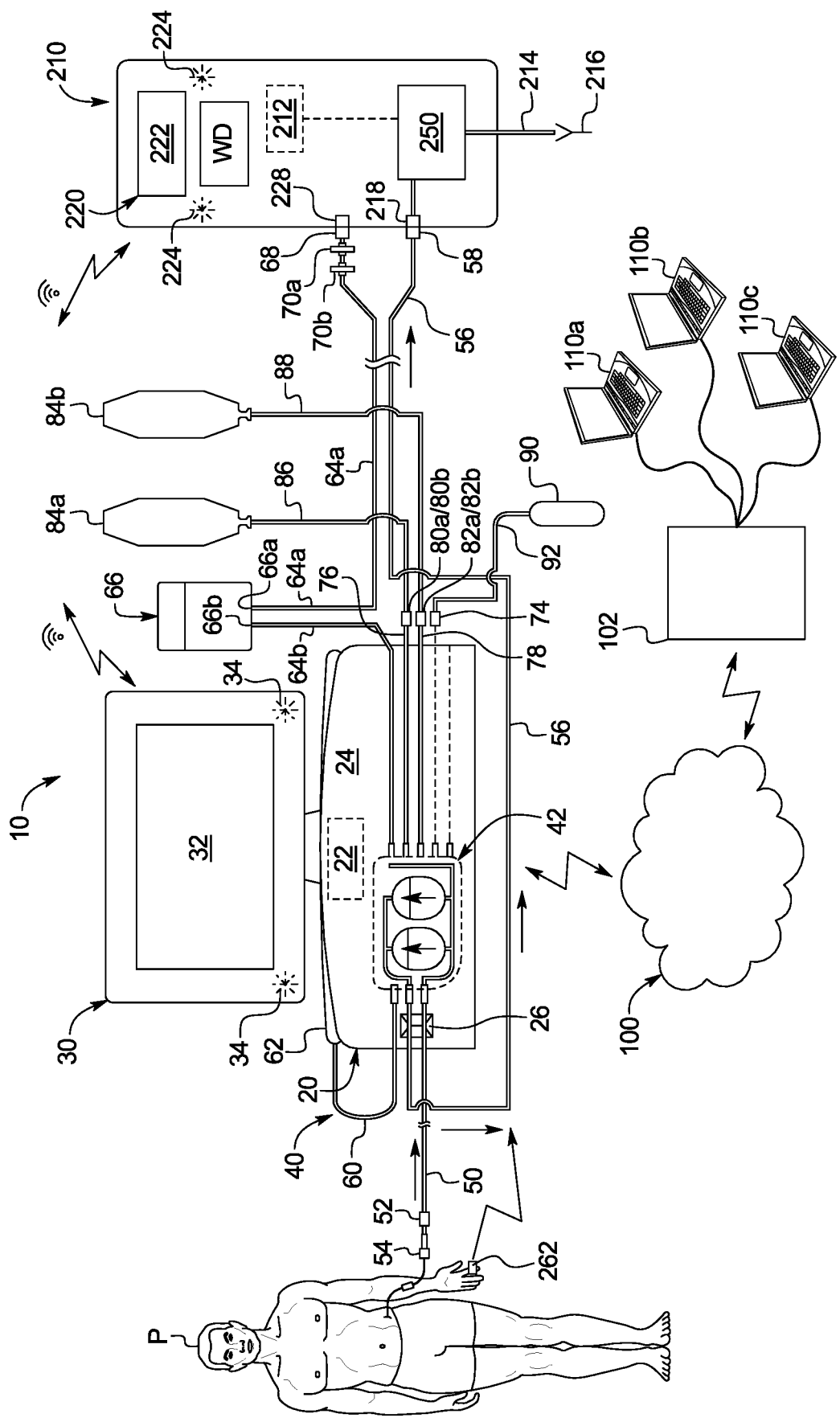
FIG. 17 is a front elevation view of a medical fluid delivery system having point of use dialysis fluid production, which operates with one embodiment for an effluent glucose sensing and insulin controlling device of the present disclosure.

MEMS affinity glucose sensor 250 in the point of use preparation version in FIG. 17 is in the illustrated embodiment located within water purifier 210, outputs electrically to control unit 212 of the water purifier, and therefore does not need wireless module 132 located along the outside of the housing of sensor 250. Control unit 212 of water purifier 210 processes the glucose level signal from MEMS affinity glucose sensor 250 and determines an amount of insulin from insulin container or bag 90 that cycler 20 should be delivered to heater/mixing bag 62 for the next patient PD fill. It should be noted that patient P is typically full of fluid from the previous treatment when beginning a current treatment. The amount of insulin to deliver is again based upon a desired insulin concentration, which is correlated to the amount of glucose sensed via device and sent to control unit 212. Knowing the desired insulin concentration and the amount of fresh pre-prepared PD fluid that is to be mixed online and delivered to heater/mixing bag 62, the amount of insulin to deliver from container or bag 90 to heater/mixing bag 62 is determined and then pumped via fluid pump chambers 44 of disposable cassette 42 to heater/mixing bag 62. In one embodiment, control unit 212 of water purifier determines the amount of insulin to pump, sends the amount to control unit 22 of cycler 20 wired or wirelessly, wherein control unit 22 uses the amount to command pump chambers 44 of disposable cassette 42 to pump the desired amount of insulin. In another embodiment, control unit 212 relays the glucose signal from bio-MEMS-glucose measuring device 250 to control unit 22 wired or wirelessly, control unit 22 determines the amount of insulin to pump and uses the amount to command pump chambers 44 of disposable cassette 42 to pump the desired amount of insulin.

Control unit 22 operates via network 100 and one or more caregiver server computer 102 to enable a doctor or clinician at one or more clinician computer 110a to 110c to view insulin usage data, e.g., on a per-treatment basis, so that the clinician may confirm that insulin is being delivered properly. The data is displayed in one embodiment on a dashboard of a website for the patient, wherein the insulin volume and concentration may be viewed. The data of the fourth primary embodiment may be displayed on the doctor or clinician website for patient P in combination with the data of the first, second and/or third primary embodiments to provide a desired combination of data. FIG. 17 also illustrates that system 10 using MEMS affinity glucose sensor 250 in one embodiment also includes glucose sensor 262, which is provided and used as described above.

Figure 18:
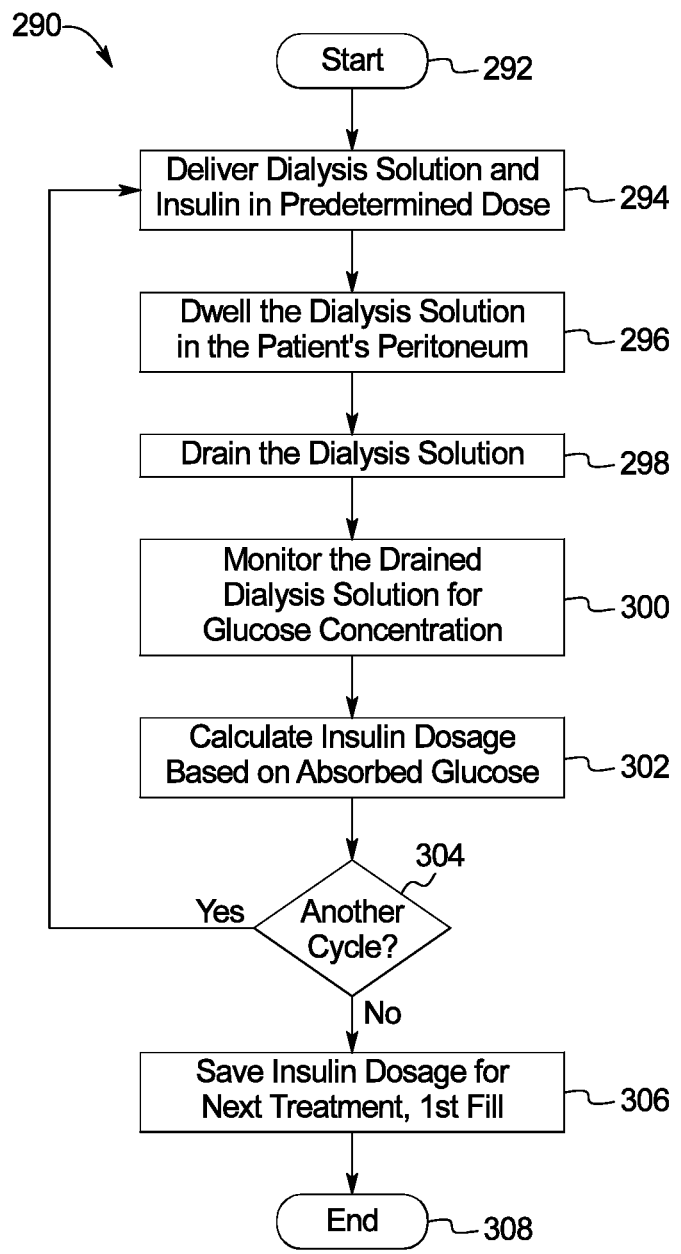
FIG. 18 is a schematic flow diagram of one embodiment of an effluent glucose sensing and insulin controlling method useable with the systems of FIGS. 15 and 16.

Referring now to FIG. 18, method 290 summarizes one embodiment for the closed loop insulin delivery just described. At oval 292, method 290 begins. At block 294, cycler 20 actuates disposable cassette 42 to (i) pull fresh dialysis fluid (pre-prepared or made at point of use) from heater bag 62 (pre-prepared) or heater/mixing bag 62 (point of use), along with a calculated dose of insulin from insulin bag or container 90 and (ii) push the heated fresh dialysis and insulin dose fluid to patient P. At block 296, the dialysis fluid is allowed to dwell within the peritoneum of patient P for a doctor/clinician prescribed amount of time. At block 298, cycler 20 actuates disposable cassette 42 to pull used dialysis fluid or effluent from the peritoneum of patient P, through patient line 50, into disposable cassette 42, and from disposable cassette 42, into drain line 56, to drain bag 96 (FIG. 14) or drain 216 at water purifier 210 (FIG. 15). MEMS affinity glucose sensor 250 is located somewhere along the drain line as illustrated in FIGS. 14 and 15. At block 300, MEMS affinity glucose sensor 250 monitors the effluent PD fluid for the patient's absorbed glucose amount or glucose concentration. At block 302, MEMS affinity glucose sensor 250 or control unit 22 of cycler 20 or control unit 212 of water purifier 210 calculates an insulin dosage based upon the glucose amount or concentration absorbed by patient P. In an embodiment, if control unit 22 of cycler 20 does not calculate the insulin dosage, then the calculated dosage is sent to control unit 22 of cycler 20.

At diamond 304, if another cycle in the current treatment exists, then method 290 returns to block 294 and control unit 22 of cycler 20 provides the next patient fill using the newly calculated dose of insulin based upon the newly monitored amount or concentration of glucose absorbed. At diamond 304, if another cycle in the current treatment does not exist, then method 290 moves to block 306 and saves the newly calculated dose of insulin based upon the newly monitored amount or concentration of glucose absorbed for the first fill of the next treatment. At oval 308, method 290 ends.

It should be appreciated that method 290 applies to a PD treatment that does not provide a "last fill" of fresh PD fluid that the patient carries through the day to the next treatment (perhaps with a midday exchange). That is, patient P leaves treatment empty. When a "last fill" is provided, then method 290 after start oval 292 proceeds instead to drain block 298 to drain the "last fill" effluent fluid from the patient, then to monitor block 300, then to calculate block 302, and then to fill fresh fluid with insulin dose block 294. The decision diamond is provided instead after fill fresh fluid with insulin dose block 294, wherein the decision is whether there is another patient drain. If so, the modified method proceeds to dwell block 296 and back through blocks 298, 300, 302 and 294. When there is no additional patient drain, the modified method ends at oval 308. Because the first step of the next treatment is to drain patient P, there is no need for insulin dosage save block 306 in the "last fill" method.

Figure 19:
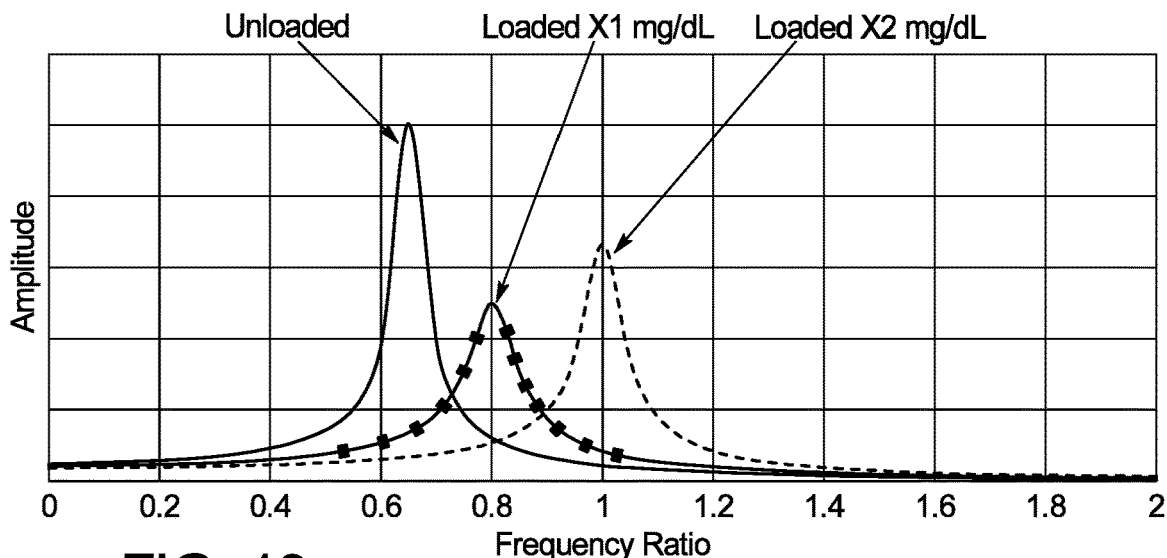
FIG. 19 is a schematic plot showing a relationship between frequency output of a MEMS affinity glucose sensor and effluent glucose level.

FIG. 19 illustrates one example relationship between glucose absorbed in the effluent fluid and frequency resonating from cantilever 260 of biosensor 258. In the example plot, effluent fluid having no absorbed glucose (continuous line) resonates at a frequency ratio of about 0.66 and yields an output amplitude that is about (i) twice as much as effluent fluid absorbed at glucose concentration×1 mg/dL (continuous line with boxes) resonating at a frequency ratio of about 0.8 and (ii) two-thirds larger than effluent fluid absorbed at glucose concentration×2 mg/dL (dashed line) resonating at a frequency ratio of about 1.0. FIG. 18 illustrates that biosensor 258 of MEMS affinity glucose sensor 250 is effective at distinguishing between different glucose concentrations present in the effluent fluid.

In one embodiment, MEMS affinity glucose sensor 250, control unit 22 or control unit 212 subtracts the glucose concentration present in the effluent fluid from an original glucose concentration of the fresh dialysis fluid delivered to patient P. The control unit is programmed to determine the amount of glucose absorbed by the patient at the end of an nth PD cycle ($P_n$) in a function as follows:

$$P_n = f(V_n, \mu, (D_{on} - D_{in})), \text{ where}$$

n=cycle number,
$V_n$=volume of PD fluid delivered for the $n^{th}$ cycle,
$\mu$=a glucose absorption coefficient (a constant determined empirically),
$D_{on}$=glucose concentration of effluent for the $n^{th}$ cycle as measured by MEMS affinity glucose sensor 250, and
$D_{in}$=original glucose concentration of the PD fluid for the $n^{th}$ cycle (PD fluids are provided in standard concentrations, such as 0.55%, 1.5%, 2.5% and 4.25%).

Based upon the amount of glucose absorbed by the patient at the end of the nth PD cycle ($P_n$), the amount of insulin to provide to the patient in the following cycle is determined in one embodiment in a function as follows:

$$I_{n+1} = f(G_I, P_n, \alpha, \beta, t), \text{ where}$$

$G_I$=initial blood glucose level before start of therapy, which is obtained in one embodiment from glucose sensor 262,
$P_n$ is calculated as discussed above,
$\alpha$ and $\beta$ are insulin absorption coefficients (constants determined empirically), and t=time.

Figure 20A:
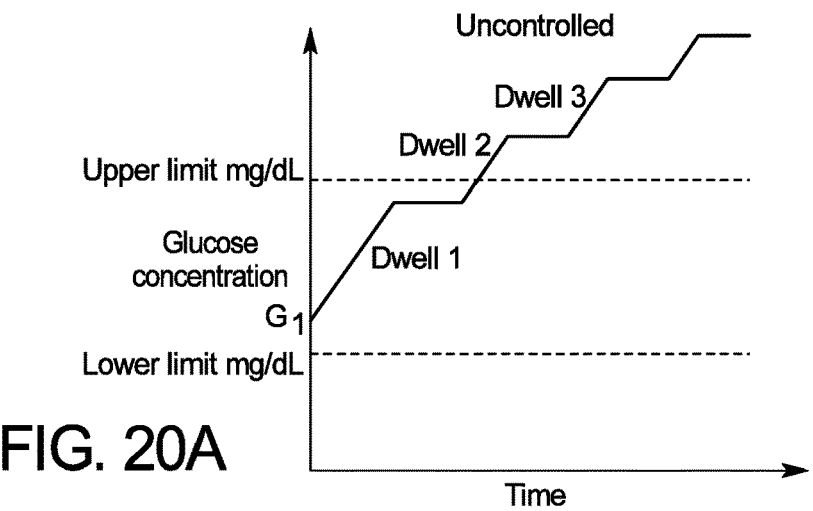
FIGS. 20A and 20B are schematic plots showing patient glucose level when uncontrolled during peritoneal dialysis treatment and controlled via the glucose feedback and insuling injection of FIGS. 15 to 18.
Figure 20B:
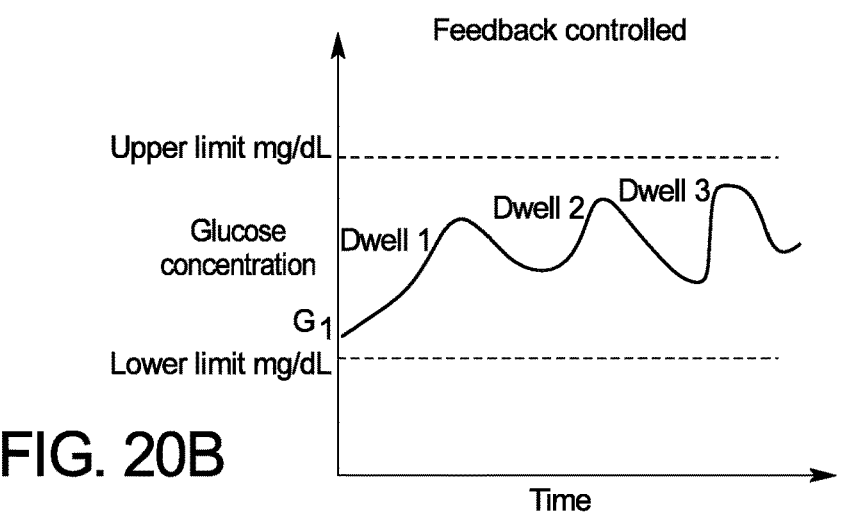

FIGS. 20A and 20B illustrate graphically how glucose levels (mg/dL) may exceed an upper threshold when uncontrolled, but reside within doctor or clinician prescribed limits when controlled using the glucose feedback and insulin injection of system 10 of FIGS. 15 to 18 having MEMS affinity glucose sensor 250. As illustrated in FIG. 20A, the glucose level (mg/dL) in patient P rises steadily over each dwell period, passing an upper threshold in the second dwell. In FIG. 20B, however, the glucose level (mg/dL) in patient P rises during the dwell periods but then falls during subsequent fill phases while insulin is injected according to the functions discussed above programmed into MEMS affinity glucose sensor 250, control unit 22 or control unit 212.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims. For example, while the four primary embodiments have been described in connection with automated peritoneal dialysis systems using cycler 20, it is contemplated that the embodiments may also be used with manual PD or continuous ambulatory peritoneal dialysis ("CAPD"). Also, while the MEMS biosensing for white blood sells and glucose molecules has been discussed in connection with a varying vibrating frequency, it is contemplated to detect other properties that may be used in a transducer to provide a sensed output property, such as voltage, including but not limited to a change in the capacitance within the microfluidic channel, or light and a change in its frequency. Moreover, while impedance monitor 230 is illustrated and described as being provided with indwelling catheter 55 of patient P, it is contemplated for any of the four primary embodiments to be implemented with the indwelling catheter.

The invention is claimed as follows:

1. A peritoneal dialysis ("PD") system comprising:
   a cycler including a pump actuator and a control unit in operable communication with the pump actuator;
   a disposable set including a disposable cassette having a pump chamber, the disposable cassette sized and arranged to be held by the cycler such that the pump chamber is in operable communication with the pump actuator, the disposable set including a patient line and a drain line extending from the disposable cassette;
   a catheter for placement within a patient's peritoneal cavity and for fluid communication with the patient line; and
   an impedance sensor operably coupled to one of the catheter, the patient line, or the drain line to sense an impedance of PD fluid residing within the patient, or removed from the patient, the sensed impedance used to detect white blood cells to form a patient peritonitis determination, the control unit configured to communicate the peritonitis determination.

2. The PD system of claim 1, wherein the sensed impedance is sent to the control unit, and wherein the control unit is configured to analyze the sensed impedance.

3. The PD system of claim 2, wherein the sensed impedance is sent to the control unit wired or wirelessly.

4. The PD system of claim 1, which includes a network and at least one doctor, or clinician, computer in communication with the control unit via the network, the control unit configured to communicate the peritonitis determination to at least one of the patient or a caregiver via a user interface of the cycler or the at least one doctor, or clinician, computer via the network.

5. The PD system of claim 1, which includes a water purifier configured to supply purified water to the disposable set, the water purifier including a water purifier control unit, wherein the sensed impedance is sent to the water purifier control unit, wherein the water purifier control unit is configured to analyze the sensed impedance, and wherein the control unit of the cycler and the water purifier control unit are in communication to allow the control unit of the cycler to communicate the peritonitis determination.

6. The PD system of claim 1, wherein the impedance sensor is located within a connector configured to couple to the catheter, the patient line, or the drain line.

7. The PD system of claim 6, wherein the connector is (i) a clamshell connector that fits around the catheter, the patient line, or the drain line, or (ii) configured to be spliced between two sections of the catheter, the patient line, or the drain line.

8. The PD system of claim 6, wherein the impedance sensor includes electrodes positioned and arranged within the catheter, the patient line, or the drain line, the connector positioned over the electrodes.

9. The PD system of claim 8, wherein the connector includes leads extending from the electrodes to (i) the control unit, (ii) a control unit of a water purifier configured to supply purified water to the disposable set, or (iii) a wireless module provided with the connector.

10. The PD system of claim 1, wherein the control unit is configured to analyze the sensed impedance of the PD fluid residing within the patient, or removed from the patient, via a frequency sweep that moves from a start frequency to a stop frequency.

11. The PD system of claim 10, wherein the frequency sweep is generated by a frequency generator provided by or operable with the control unit.

12. The PD system of claim 10, wherein the control unit is configured to take an impedance measurement at two or more frequencies of the frequency sweep.

13. The PD system of claim 10, wherein the frequency sweep enables fluid having white blood cells and residing within the patient, or removed from the patient, to be determined by measuring, over at least a portion of the frequency sweep, higher impedances for the fluid having white blood cells than impedances for fluid not having white blood cells.

14. The PD system of claim 13, wherein the impedances for fluid not having white blood cells (i) are determined based on set standard impedances, or (ii) are determined based on impedances established for the patient.

15. The PD system of claim 10, wherein the frequency sweep enables fluid having white blood cells and residing within the patient, or removed from the patient, to be distinguished from fluid having fibrin, wherein the fluid having fibrin yields higher impedances over at least a portion of the frequency sweep than the fluid having white blood cells.

16. The PD system of claim 1, wherein the peritonitis determination is a first peritonitis indicator, and the control unit is configured to obtain at least one different peritonitis indicator useable in combination with the first peritonitis indicator to form an overall peritonitis determination.

17. The PD system of claim 16, wherein the at least one different peritonitis indicator useable in combination with the first peritonitis indicator is obtained from at least one of a patient effluent PD fluid temperature sensor or a white blood cell biosensor.

18. The PD system of claim 1, wherein the peritonitis determination is provided in combination with an insulin injection made using feedback from a patient effluent glucose biosensor.

19. A peritoneal dialysis ("PD") system comprising:
a cycler including a pump actuator and a control unit in operable communication with the pump actuator;
a disposable set including a pump portion sized and arranged to be held by the cycler such that the pump portion is in operable communication with the pump actuator, the disposable set including a patient line and a drain line;
a catheter for placement within a patient's peritoneal cavity and for fluid communication with the patient line; and
an impedance sensor operably coupled to one of the catheter, the patient line, or the drain line to sense an impedance of PD fluid residing within the patient, or removed from the patient, the sensed impedance used to detect white blood cells to form a patient peritonitis determination.

20. A peritoneal dialysis ("PD") system comprising:
a pump actuator and a control unit in operable communication with the pump actuator;
a disposable set including a pump portion sized and arranged to be placed in operable communication with the pump actuator, the disposable set including a patient line and a drain line;
a catheter for placement within a patient's peritoneal cavity and for fluid communication with the patient line; and
an impedance sensor operably coupled to one of the catheter, the patient line, or the drain line to sense PD fluid residing within the patient, or removed from the patient, over a frequency sweep that moves from a start frequency to a stop frequency, the sensed impedance frequency sweep used to detect white blood cells to form a patient peritonitis determination.

* * * * *